US007109170B2

(12) United States Patent
Bajaj et al.

(10) Patent No.: US 7,109,170 B2
(45) Date of Patent: Sep. 19, 2006

(54) REGION OF FACTOR IXA PROTEASE DOMAIN THAT INTERACTS WITH FACTOR VIIIA AND METHODS THEREFOR

(75) Inventors: Paul S. Bajaj, St. Louis, MO (US); Amy E. Schmidt, St. Louis, MO (US)

(73) Assignee: Saint Louis University, St. Louis, MO (US)

( * ) Notice: Subject to any disclaimer, the term of this patent is extended or adjusted under 35 U.S.C. 154(b) by 305 days.

(21) Appl. No.: 10/662,784

(22) Filed: Sep. 15, 2003

(65) Prior Publication Data

US 2004/0110688 A1 Jun. 10, 2004

Related U.S. Application Data

(63) Continuation-in-part of application No. 09/584,866, filed on Jun. 1, 2000, now Pat. No. 6,624,289.

(60) Provisional application No. 60/139,391, filed on Jun. 16, 1999.

(51) Int. Cl.
*A61K 38/10* (2006.01)
*A61K 38/08* (2006.01)

(52) U.S. Cl. ............................ 514/13; 514/14; 514/15; 514/16; 514/17; 530/326; 530/327; 530/328; 530/329

(58) Field of Classification Search ...................... None
See application file for complete search history.

(56) References Cited

U.S. PATENT DOCUMENTS

| | | | | |
|---|---|---|---|---|
| 5,639,641 | A | * | 6/1997 | Pedersen et al. ............ 435/69.6 |
| 5,639,863 | A | * | 6/1997 | Dan ......................... 530/388.8 |
| 5,914,110 | A | * | 6/1999 | Holmes et al. ........... 424/133.1 |
| 5,932,706 | A | * | 8/1999 | Mertens et al. .............. 530/413 |
| 6,624,289 | B1 | * | 9/2003 | Bajaj .......................... 530/328 |

FOREIGN PATENT DOCUMENTS

| | | |
|---|---|---|
| WO | WO 93/09804 | 5/1993 |
| WO | WO 94/25482 | 11/1994 |
| WO | WO9526979 | * 10/1995 |

OTHER PUBLICATIONS

Mathur et al., Protease and EGF1 domains of factor IXa play distinct roles in binding to factor VIIIa, J. Biol. Chem., 1999, 274(26): 18477-18486.
Yoshitake et al., Nucleotide sequence of the gene for human factor IX (antihemophilic factor B), Biochemistry, 1985, 24: 3736-3750.
DiScipio et al., Activation of human factor IX (Christmas factor), J. Clin. Invest., 1978, 61: 1528-1538.
Davie et al., The coagulation cascade: initiation, maintenance, and regulation, Biochemistry, 1991, 30: 10363-10370.
Brandstetter et al., X-ray structure of clotting factor IXa: active site and module structure related to Xase activity and hemophilia B., Proc. Natl. Acad. Sci. USA, 1995, 92: 9796-9800.
Banner et al., The crystal structure of the complex of blood coagulation factor VIIa with soluable tissue factor, Nature, 1996, 380: 41-46.
Sabharwal et al., Interaction of calcium with native and decarboxylated human factor X. Effect of proteolysis in the autolysis loop on catalytic efficiency and factor Va binding, J. Biol. Chem., 1997, 272: 22037-22045.
Rao et al., The structure of a Ca(2+)-binding epidermal growth factor-like domain: its role in protein-protein interactions, Cell, 1995, 82: 131-141.
Bajaj et al., Antibody-probed conformational transitions in the protease domain of human factor IX upon calcium binding and zymogen activation: putative high-affinity Ca(2+)-binding site in the protease domain, Proc. Natl. Acad. Sci. USA; 1992, 89: 152-156.
Freedman et al., Identification of the phospholipid binding site in the vitamin K-dependent blood coagulation protein factor IX, J. Biol. Chem., 1996, 271: 16227-16236.
Zhong et al., First epidermal growth factor-like domain of human blood coagulation factor IX is required for its activation by factor VIIa/tissue factor but not by factor XIa, Proc. Natl. Acad. Sci. USA, 1994, 91: 3574-3578.
Lenting et al., Ca2+ binding to the first epidermal growth factor-like domain of human blood coagulation factor IX promotes enzyme activity and factor VIII light chain binding, J. Biol. Chem., 1996, 271: 25332-25337.
Ahmed et al., The role of the second growth-factor domain of human factor IXa in binding to platelets and in factor-X activation, Biochem. J., 1995, 310: 427-431.
Astermark et al., The gamma-carboxyglutamic acid and epidermal growth factor-like modules of factor IXa beta. Effects on the serine protease module and factor X activation, J. Biol. Chem., 1994, 269: 3682-3689.

(Continued)

*Primary Examiner*—Robert A. Wax
(74) *Attorney, Agent, or Firm*—Thompson Coburn, LLP

(57) ABSTRACT

Novel polypeptides or derivatives comprising the factor VIIIa binding site on factor IXa are disclosed. The novel polypeptides or derivatives have anti-coagulation activity. Nucleic acids encoding those polypeptides are also disclosed. Methods for identifying an agent having anti-coagulation activity are also disclosed. These methods comprise determining whether the agent displaces the polypeptide or derivative from its factor VIIIa binding site. The agent identified in these methods is also useful in methods for treating a patient to prevent thrombosis. The treatment methods comprise administration of the agent to the patient. Additional methods are also disclosed for treating a patient to prevent thrombosis, comprising treating the patient with a polypeptide or derivative comprising the factor VIIIa binding site on factor IXa. Methods of preventing coagulation in a blood sample are also disclosed, comprising adding the polypeptides or derivatives described above to the blood sample. Methods of detecting factor VIIIa in a sample are also disclosed. Those methods comprise contacting the sample with the above-described polypeptide or derivative, wherein the polypeptide or derivative also comprises a covalently attached detectable moiety, then determining whether the polypeptide or derivative is binding factor VIIIa from the sample.

22 Claims, 15 Drawing Sheets

OTHER PUBLICATIONS

O'Brien et al., Localization of factor IXa and factor VIIIa interactive sites, J. Biol. Chem., 1995, 270: 27087-27092.

Bajaj et al., Human factor IX and factor IXa, Methods Enzymol, 1993, 222: 96-128.

Mathur et al., Interaction of factor IXa with factor VIIIa. Effects of protease domain Ca2+ binding site, proteolysis in the autolysis loop, phospholipids, and factor X, J. Biol. Chem., 1997, 272: 23418-23426.

Hamaguchi et al., The role of amino-terminal residues of the heavy chain of factor IXa in the binding of its cofactor, factor VIIIa, Blood, 1994, 84: 1837-1842.

Ripka et al., Peptidomimetic design, Current Opin. Chem. Biol., 1998, 2(4): 441-452.

Wood et al., Expression of active human factor VIII from recombinant DNA clones, Nature, 1984, 312: 330-337.

Vehar et al., Structure of human factor VIII, Nature, 1984, 312: 337-342.

Bajaj et al., A simplified procedure for purification of human prothrombin, factor IX and factor X, Prep. Biochem., 1981, 11: 397-412.

Zhong and Bajaj, A PCR-based method for site-specific domain replacement that does not require restriction recognition sequences, Biotechniques, 1993, 15: 874-878.

Usharani et al., Characterization of three abnormal factor IX variants (Bm Lake Elsinore, Long Beach, and Los Angeles) of hemophilia-evidence for defects affecting the latent catalytic site, J. Clin. Invest., 1985, 75: 76-83.

Link and Castellino, The activation of bovine factor X by bovine factor Xa, Arch. Biochem. Biophys., 1982, 215: 215-221.

Van Dieijen et al., The role of phospholipids and factor VIIIa in the activation of bovine factor X, J. Biol. Chem. 1981, 256: 3433-3442.

Fay and Koshibu, The A2 subunit of factor VIIIa modulates the active site of factor IXa, J. Biol. Chem., 1998, 273: 19049-19054.

Krishnaswamy, The interaction of human factor VIIa with tissue factor, J. Biol. Chem., 1992, 267: 23696-23706.

Halfman, Concentrations of binding protein and labeled analyte that are appropriate for measuring at any analyte concentration range in radioimmunoassays, Meth. Enzymol., 1981, 74: 481-508.

Bylund and Toews, Radioligand binding methods: practical guide and tips, Am. J. Physiol., 1993, 265: L421-L42.

Rees et al., The role of beta-hydroxyaspartate and adjacent carboxylate residues in the first EGF domain of human factor XI, EMBO J., 1988, 7: 2053-2061.

Hughes et al., Tyrosine 69 of the first epidermal growth factor-like domain human factor IX is essential for clotting activity, J. Biol. Chem., 1993, 268: 17727-17733.

Frazier et al., Mapping of monoclonal antibodies to human factor IX, Blood, 1989, 74: 971-977.

Ludwig et al., Hemophilia B caused by five different nondeletion mutations in the protease domain of factor IX, Blood, 1992, 79: 1225-1232.

Giannelli et al., Haemophilia B: database of point mutations and short additions and deletions—eighth edition, Nucleic Acids Res., 1998, 26: 265-268.

Mather et al., The 2.8 A crystal structure of Gla-domainless activated protein C, EMBO J., 1996, 15: 6822-6831.

Bajaj et al., Synthesis and expression of tissue factor pathway inhibitor by serum-stimulated fibroblasts, vascular smooth muscle cells and cardiac myocytes, Thrombos. Haemostas, 1999, 82: 1663-1672.

Chang et al., Changing residue 338 in human factor IX from arginine to alanine causes an increase in catalytic activity, J. Biol. Chem., 1998, 273: 12089-12094.

Lin et al., Expression and characterization of human factor IX and factor IX-factor X chimeras in mouse C127 cells, J. Biol. Chem., 1990, 265: 144-150.

Chang et al., Replacing the first epidermal growth factor-like domain of factor IX with that of factor VII enhances activity in vitro and in canine hemophilia B, J. Clin. Invest., 1997, 100: 886-892.

Spitzer et al., Factor IX Hollywood: substitution of Pro55 by Ala in the first epidermal growth factor-like domain, Blood, 1990, 76: 1530-1537.

McCord et al., Characterization of the functional defect n factor IX Alabama, J. Biol. Chem., 1990, 265: 10250-10254.

Christophe et al., Blood coagulation factor IX residues Glu78 and Arg94 provide a link between both epidermal growth factor-like domains that is crucial in the interaction with factor VIII light chain, J. Biol. Chem., 1998, 273: 222-227.

Larson et al., Structural integrity of the gamma-carboxyglutamic acid domain of human blood coagulation factor IXa is required for its binding to cofactor VIIIa, J. Biol. Chem., 1996, 271: 3869-3876.

Sabharwal et al., High affinity Ca(2+)-binding site in the serine protease doma of human factor VIIas and its role in tissue factor binding and development of catalytic activity, J. Biol. Chem., 1995, 270: 15523-15530.

Bajaj et al., A monoclonal antibody to factor IX that inhibits the factor VII:Ca potentiation of factor X activation, J. Biol. Chem., 1985, 260: 11574-11580.

* cited by examiner

SEQUENCE LISTING

<160> NUMBER OF SEQ ID NOS: 8

<210> SEQ ID NO 1
<211> LENGTH: 9
<212> TYPE: PRT
<213> ORGANISM: Homo sapiens

<400> SEQUENCE: 1

Leu Val Asp Arg Ala Thr Cys Leu Arg
1               5

<210> SEQ ID NO 2
<211> LENGTH: 4
<212> TYPE: PRT
<213> ORGANISM: Homo sapiens

<400> SEQUENCE: 2

Asp Arg Ala Thr
1

<210> SEQ ID NO 3
<211> LENGTH: 5
<212> TYPE: PRT
<213> ORGANISM: Homo sapiens

<400> SEQUENCE: 3

Ala Asp Arg Ala Thr
1               5

<210> SEQ ID NO 4
<211> LENGTH: 5
<212> TYPE: PRT
<213> ORGANISM: Homo sapiens

<400> SEQUENCE: 4

Asp Arg Ala Thr Ala
1               5

<210> SEQ ID NO 5
<211> LENGTH: 7
<212> TYPE: PRT
<213> ORGANISM: Homo sapiens

<400> SEQUENCE: 5

Arg Leu Met Thr Gln Asp Gln
1               5

<210> SEQ ID NO 6
<211> LENGTH: 5
<212> TYPE: PRT
<213> ORGANISM: Homo sapiens

<400> SEQUENCE: 6

Tyr Asn Ser Lys Leu
1               5

<210> SEQ ID NO 7
<211> LENGTH: 6
<212> TYPE: PRT
<213> ORGANISM: Homo sapiens

<400> SEQUENCE: 7

```
Ile Glu Pro Val Lys Asp
1               5

<210> SEQ ID NO 8
<211> LENGTH: 7
<212> TYPE: PRT
<213> ORGANISM: Homo sapiens

<400> SEQUENCE: 8

Val Pro His Asn Glu Ser Glu
1               5
```

REGION OF FACTOR IXA PROTEASE DOMAIN THAT INTERACTS WITH FACTOR VIIIA AND METHODS THEREFOR

RELATED APPLICATION

This application is a continuation-in-part of U.S. patent application Ser. No. 09/584,866, filed Jun. 1, 2000, now U.S. Pat. No. 6,624,289. application Ser. No. 09/584,866 claims priority to U.S. provisional patent application Ser. No. 60/139,391, filed Jun. 16, 1999, which is now abandoned—all of which are incorporated herein by reference.

REFERENCE TO GOVERNMENT GRANT

This invention was made with government support under NIH Grant No. HL 36365. The government has certain rights in the invention.

BACKGROUND OF THE INVENTION (1) Field of the Invention

This invention relates generally to the prevention of coagulation. More particularly, this invention relates to compositions and methods for preventing coagulation by inhibiting binding of factor IXa to factor VIIIa, and applications utilizing these compositions and methods, including treating patients in need of anti-coagulants, preventing coagulation in blood samples, and detecting factor VIIIa.

(2) Description of the Related Art

Two common causes of abnormal bleeding are deficiencies of factor VIII (hemophilia A) or factor IX (hemophilia B). Factor IX, a vitamin K-dependent protein, is synthesized by hepatocytes as a precursor molecule of 461 residues containing a 28 residue signal propeptide and an 18 residue leader propeptide (Yoshitake et al., 1985, *Biochemistry* 24, 3736–3750). During biosynthesis, the nascent protein undergoes several posttranslational modifications, resulting in a single-chain protein consisting of 415 amino acids and containing 17% carbohydrate by weight (DiScipio et al., 1978, *J. Clin. Invest.* 61, 1528–1538). The mature protein circulates in blood as a zymogen of Mr 57,000.

Factor IX is activated during physiologic clotting to the two-chain, disulfide-linked serine protease, factor IXa, by VIIa/$Ca^{2+}$/tissue factor (TF) or by factor XIa/$Ca^{2+}$ (Davie et al., 1991, *Biochemistry* 29, 10363–10370). The domain organization of factor IXa is similar to those of the other two enzymes (factors VIIa and Xa) involved in the TF-induced coagulation and to that of an anticoagulant enzyme termed activated protein C. The light chain of IXa consists of an amino-terminal γ-carboxyglutamic acid domain ("Gla domain", residues 1–40 out of which 12 are γ-carboxyglutamic acid residues), a short hydrophobic segment (residues 41–46), and two epidermal growth factor (EGF)-like domains (EGF1 residues 47–85, and EGF2 residues 86–127) whereas the heavy chain contains the carboxy-terminal serine protease domain with trypsin-like specificity (Id.; Brandstetter et al., 1995, *Proc. Natl. Acad. Sci. USA* 92, 9796–9800). Activation peptide (AP) of residues 145–180 which is released upon conversion of factor IX to IXa is rich in carbohydrate and is the least conserved region in IX from different species (Sarkar et al., 1990, *Genomics* 6, 133–134). Factor IXa hence formed converts factor X to Xa in the coagulation cascade; for a biologically significant rate, this reaction requires $Ca^{2+}$, phospholipid and factor VIIIa.

Based upon the crystal structure of the Gla domain of factor VIIa (Banner et al., 1996, *Nature* 380, 41–46) and the $Ca^{2+}$-binding properties of factor X (Sabharwal et al., 1997, *J. Biol. Chem.* 272, 22037–22045.), it would appear that this domain in IXa possesses several low to intermediate affinity $Ca^{2+}$-binding sites. In addition, the EGF1 and the protease domain each possess one high affinity $Ca^{2+}$-binding site (Rao et al., 1995, *Cell* 82, 131–141; Bajaj et al., 1992, *Proc. Natl. Acad. Sci. USA* 89, 152–156). The $Ca^{2+}$-loaded conformer of the Gla domain binds to phospholipid vesicles (Freedman et al., 1996, *J. Biol. Chem.* 271, 16227–16236) and the EGF 1 domain of IX is required for its activation by VIIa/$Ca^{2+}$/TF (Zhong et al., 1994, *Proc. Natl. Acad. Sci. USA* 91, 3574–3578). Further, $Ca^{2+}$-binding to the EGF1 domain has been reported to promote enzyme activity and factor VIIIa binding (Lenting et al., 1996, *J. Biol. Chem.* 271, 25332–25337). The role of the EGF2 domain is not clear but may be involved in binding to platelets and in factor X activation (Ahmed et al., 1995, *Biochem. J.* 310, 427–431). Finally, the protease domain is thought to play a primary role in binding to factor VIIIa (Astermark et al., 1994, *J. Biol. Chem.* 269, 3682–3689; O'Brien et al., 1995, *J. Biol. Chem.* 270, 27087–27092; Bajaj et al., 1993, *Methods Enzymol.* 222, 96–128).

Recently, it has been demonstrated that mutations in the protease domain $Ca^{2+}$-binding ligands decrease the affinity of factor IXa for factor VIIIa by ~15-fold and that proteolysis at R318-S319 [residues 150–151 in the chymotrypsin numbering system] in the autolysis loop results in a further decrease in this interaction by ~8-fold (Mathur et al., 1997, *J. Biol. Chem.* 272, 23418–23426). Since residues in the protease domain $Ca^{2+}$-binding loop as well as those in the autolysis loop may not directly participate in binding to factor VIIIa (Hamaguchi et al., 1994, *Blood* 84, 1837–1842), it can be hypothesized that $Ca^{2+}$ binding to the protease domain and integrity of the autolysis loop stabilize yet another region in this domain of factor IXa that directly interacts with factor VIIIa.

The identification of the factor VIIIa binding site on factor IXa would be useful for identifying agents with anti-coagulation activity, as well as for designing treatments which prevent excessive thrombosis in a patient, and preventing coagulation of blood samples.

SUMMARY OF THE INVENTION

In accordance with the present invention, the inventor herein has succeeded in identifying a crucial region in factor IXa which binds to factor VIIIa. Compositions which comprise critical amino acids of this region, but which do not activate factor X, bind to factor VIIIa, preventing the binding of factor IXa, thus preventing coagulation. These compositions can thus be used to prevent thrombosis in patients in need thereof. The compositions can also be used to prevent coagulation in a blood sample, and to detect and quantify factor VIIIa in a sample.

Thus, one embodiment of the present invention is directed to a polypeptide, or derivative thereof, including peptidomimetics and nonpeptidomimetics, comprising $DRX_{aa}T$ or derivatives, where $X_{aa}$ is any amino acid, wherein the polypeptide or derivative has anti-coagulation activity. This polypeptide or derivative comprises the three amino acids essential to the factor VIIIa binding site in factor IXa. Preferably, this polypeptide, or derivative binds to factor VIIIa but does not activate factor X. The polypeptide or derivative also preferably comprises from 4 to 20 contiguous amino acids. Preferred polypeptides or derivatives comprise SEQ ID NO:2 (DRAT) or SEQ ID NO:1 (LVDRATCLR), which are sequences in the factor VIIIa binding site in factor IXa. Preferably, the polypeptide consists essentially of SEQ ID NO:2 (DRAT). More preferably, the polypeptide consists of SEQ ID NO:2 (DRAT).

Another embodiment of the present invention is directed to an isolated and substantially purified polypeptide or derivative thereof, comprising DRX$_{aa}$T where X$_{aa}$ is any amino acid other than alanine. Preferred polypeptides or derivatives here have from 4 to 20 amino acids. The polypeptide or derivative also preferably binds to factor VIIIa but does not activate factor X.

Another embodiment of the invention is directed to an isolated and substantially purified polypeptide or derivative thereof consisting of from 4 to 9 amino acids, wherein the polypeptide is capable of inhibiting the activation of coagulation factor X in the presence of coagulation factor VIIIa, and the polypeptide is derived from helix 330 of factor IXa. Preferred polypeptides consist of SEQ ID NO:2 (DRAT), SEQ ID NO:5 (LVX$_{aa1}$X$_{aa2}$AT), wherein X$_{aa1}$ is either aspartic acid or tyrosine and X$_{aa2}$ is either arginine or glutamine, or SEQ ID NO:9 (LVDRATX$_{aa}$LR), wherein X$_{aa}$ is any amino acid except cysteine. More preferred polypeptides consist of SEQ ID NO:2 (DRAT), SEQ ID NO:6 (LVDRAT), SEQ ID NO:7 (LVYRAT), SEQ ID NO:8 (LVDQAT) or SEQ ID NO:10 (LVDRATALR). The most preferred polypeptide consists of SEQ ID NO:2 (DRAT).

In an additional embodiment, the present invention is directed to an isolated and purified nucleic acid molecule, comprising a nucleotide sequence encoding a polypeptide comprising DRX$_{aa}$T, where X$_{aa}$ is any amino acid, wherein the polypeptide or derivative has anti-coagulation activity, or the complement thereof. Preferably, the polypeptide comprises SEQ ID NO:1 (LVDRATCLR) or SEQ ID NO:2 (DRAT).

In an additional embodiment, the present invention is directed to an isolated and purified nucleic acid molecule, comprising a nucleotide sequence encoding a polypeptide or derivative thereof that has anti-coagulation activity, or the complement thereof. The polypeptide comprises SEQ ID NO:2 (DRAT), SEQ ID NO:5 (LVX$_{aa1}$X$_{aa2}$AT), wherein X$_{aa1}$ is either aspartic acid or tyrosine and X$_{aa2}$ is either arginine or glutamine, or SEQ ID NO:9 (LVDRATX$_{aa}$LR), wherein X$_{aa}$ is any amino acid except cysteine. Preferably, the nucleic acid molecules encodes a polypeptide comprising SEQ ID NO:2 (DRAT), SEQ ID NO:6 (LVDRAT), SEQ ID NO:7 (LVYRAT), SEQ ID NO:8 (LVDQAT) or SEQ ID NO:10 (LVDRATALR). The most preferred nucleic acid encodes a polypeptide comprising SEQ ID NO:2 (DRAT).

Additionally, the present invention is directed to a method for identifying an agent having anti-coagulation activity. The method comprises determining whether a candidate agent displaces the binding of a polypeptide comprising SEQ ID NO:2 (DRAT), SEQ ID NO:5 (LVX$_{aa1}$X$_{aa2}$AT), wherein X$_{aa1}$ is either aspartic acid or tyrosine and X$_{aa2}$ is either arginine or glutamine, or SEQ ID NO:9 (LVDRATX$_{aa}$LR), wherein X$_{aa}$ is any amino acid except cysteine from factor VIIIa, wherein the polypeptide preferably has from 4 to 20 amino acids, but may be longer, up to and including the entire factor IXa molecule. Preferably, the polypeptide is a labeled polypeptide and the determining step comprises detecting the labeled polypeptide displaced from factor VIIIa. Preferred labels comprise a radioactive or a fluorescent moiety.

In an additional embodiment, the present invention is directed to a method of treatment to prevent thrombosis in a patient in need thereof. The method comprises administering to the patient a polypeptide or derivative thereof comprising DRX$_{aa}$T, where X$_{aa}$ is any amino acid, wherein the polypeptide or derivative has anti-coagulation activity. The preferred polypeptide or derivative binds to factor VIIIa but does not activate factor X. More preferably, the polypeptide has from 4 to 20 amino acids. Most preferred polypeptide comprise SEQ ID NO:2 (DRAT) or SEQ ID NO:1 (LVDRATCLR). In another embodiment, the polypeptide comprises SEQ ID NO:5 (LVX$_{aa1}$X$_{aa2}$AT), wherein X$_{aa1}$ is either aspartic acid or tyrosine and X$_{aa2}$ is either arginine or glutamine, or SEQ ID NO:9 (LVDRATX$_{aa}$LR), wherein X$_{aa}$ is any amino acid except cysteine. Preferably, the nucleic acid molecules encodes a polypeptide comprising SEQ ID NO:2 (DRAT), SEQ ID NO:6 (LVDRAT), SEQ ID NO:7 (LVYRAT), SEQ ID NO:8 (LVDQAT) or SEQ ID NO:10 (LVDRATALR). The most preferred nucleic acid encodes a polypeptide comprising SEQ ID NO:2 (DRAT). An 4antibody that specifically binds to these sequences would also be expected to prevent thrombosis. Such an antibody could also be utilized in place of the above polypeptides or derivatives in the embodiments described below.

In still another embodiment, the present invention is directed to a method of treatment to prevent thrombosis in a patient in need thereof. The method comprises selecting an agent having anti-coagulation activity, wherein the selecting comprises testing the agent for activity in displacing the binding of Factor IXa from Factor VIIIa without activating Factor X, and administering the agent to the patient.

An additional embodiment of the present invention is a method of preventing coagulation in a blood sample. The method comprises adding to the sample, in sufficient quantity to prevent coagulation, a polypeptide or derivative thereof comprising DRX$_{aa}$T, where X$_{aa}$ is any amino acid, wherein the polypeptide or derivative has anti-coagulation activity. A preferred polypeptide or derivative is capable of binding to factor VIIIa but does not activate factor X. More preferably, the polypeptide or derivative has from 4 to 20 amino acids or derivatives. Most preferably, the polypeptide or derivative comprises SEQ ID NO:2 (DRAT) or SEQ ID NO: 1 (LVDRATCLR). In another embodiment, the polypeptide comprises SEQ ID NO:5 (LVX$_{aa1}$X$_{aa2}$AT), wherein X$_{aa1}$ is either aspartic acid or tyrosine and X$_{aa1}$ is either arginine or glutamine, or SEQ ID NO:9 (LVDRATX$_{aa}$LR), wherein X$_{aa}$ is any amino acid except cysteine. Preferably, the nucleic acid molecules encodes a polypeptide comprising SEQ ID NO:2 (DRAT), SEQ ID NO:6 (LVDRAT), SEQ ID NO:7 (LVYRAT), SEQ ID NO:8 (LVDQAT) or SEQ ID NO:10 (LVDRATALR). The most preferred nucleic acid encodes a polypeptide comprising SEQ ID NO:2 (DRAT).

Additionally, the present invention is directed to a method of detecting factor VIIIa in a sample. The method comprises (a) contacting the sample with a polypeptide or derivative thereof comprising a covalently attached detectable moiety and DRX$_{aa}$T, where X$_{aa}$ is any amino acid, and wherein the polypeptide or derivative has anti-coagulation activity, and (b) determining whether the polypeptide or derivative is binding factor VIIIa from the sample. Preferably, the detectable moiety is radioactive or fluorescent.

DETAILED DESCRIPTION OF THE INVENTION

Figure 1A:
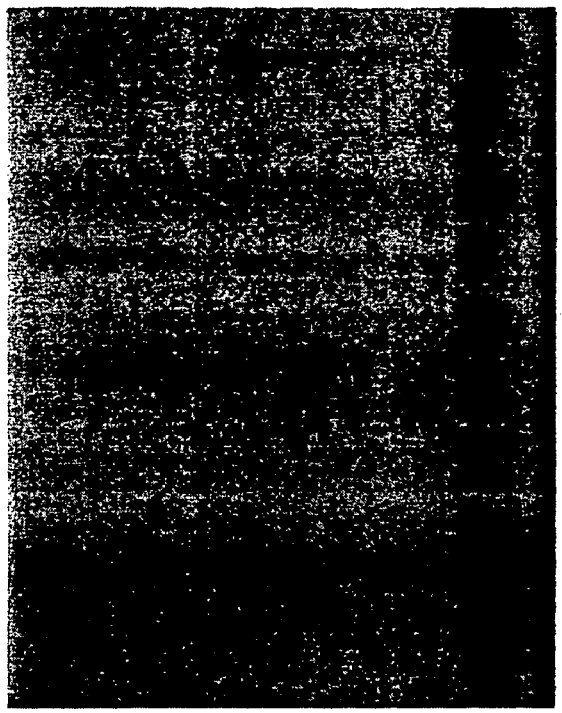
FIG. 1A depicts an SDS gel electrophoretic analysis of various protease domain mutants of Factor IX, and wild-type Factor IX (WT) before activation with factor XIa and Ca$^{2+}$, where approximately 2.3 µg of protein was applied to each lane.

In accordance with the present invention, it has been discovered that factor X can be inhibited from factor IXa activation by the introduction of compositions capable of binding to factor VIIIa at the factor IXa binding site. The compositions comprise polypeptides or polypeptide derivatives which comprise certain residues (or derivatives) of the factor VIIIa binding site on factor IX. The utilization of these compositions in vitro or in vivo effectively inhibits the coagulation cascade.

The factor VIIIa binding site on factor IXa is in the 330 helix of factor IXa and has the sequence

330-LVDRATCLR-338 (SEQ ID NO:1)

which corresponds to residues 162–170 using the chymotrypsin numbering system. However, within this sequence, residues 332 (D), 333 (R), and 335(T) are most crucial, since those resides are present in the hydrophilic portion of the helix in this binding site and are thus expected to interact most predominantly with factor VIIIa. Thus, the sequence DRX$_{aa}$T, where X$_{aa}$ is any amino acid or derivative, would bind to factor VIIIa. When this sequence is a part of a polypeptide or derivative which is unable to activate factor X (e.g., by not having active serine protease activity), the polypeptide or derivative will bind factor VIIIa at the factor IXa binding site and prevent wild-type factor IXa from binding, thus preventing coagulation and factor X activation. This would be expected based on the results presented in the Example 1 herein, since, when the factor IXa 330 helix was replaced with the corresponding homologous region from factor VII, the factor IXa-VII chimera could not induce activation of factor X, even at high concentrations (Table 1). Also, replacement of the D and the R of this helix with other amino acids severely reduced or abolished the ability of factor IXa to activate factor X (Table 1).

Thus, in one embodiment, the present invention provides a composition that comprises a polypeptide or derivative that includes the sequence DRX$_{aa}$T, wherein X$_{aa}$ is independently any amino acid, or a derivative thereof. Since this composition has the crucial amino acid residues present in factor IXa as D332, R333, and T335, or derivatives of those resides, it will bind to factor VIIIa at the factor IXa binding site and prevent coagulation and factor X activation. Preferred compositions comprise the entire 9-mer binding site LVDRATCLR (SEQ ID NO:1) or derivatives, or the 4-mer within that sequence which contains the three crucial amino acid residues, DRAT (SEQ ID NO:2). The most preferred polypeptides have 4–20 amino acid residues or derivatives, but can comprise much larger sequences, including, for example, factor IXa which has been altered to eliminate its serine protease activity.

In another embodiment, the polypeptide comprises SEQ ID NO:5 (LVXX$_{12}$AT), wherein X$_1$ is either D or Y, and X$_2$ is either R or Q, SEQ ID NO:6 (LVDRAT), SEQ ID NO:7 (LVYRAT), SEQ ID NO:8 (LVDQAT), SEQ ID NO:9 (LVDRATXLR), wherein X is any amino acid other than C, or SEQ ID NO:10 (LVDRATALR).

As used herein, the term "derivative" includes any nonpeptide compound, including peptidomimetics or nonpeptidomimetics, that can substitute for a particular amino acid or polypeptide. Based on the structural features of the critical amino acid sequence of the peptides of the present invention that permit the binding of the peptide to factor VIIIa, one can develop these non-peptide derivatives that are capable of binding to factor VIIIa and preventing coagulation. Thus, a non-peptide derivative includes any non-peptide chemical compound that can bind to factor VIIIa and prevent coagulation.

The techniques for development of peptidomimetics and nonpeptidomimetics are well known in the art. See for example, Navia and Peattie, 1993, *Trends Pharm. Sci.* 14:189–195; Ripka et al., 1998, *Curr. Opin. Chem. Biol.* 2:441–452; Kieber-Emmons et al., *Curr. Opin. Biotechnol.* 8:435–441; Freidinger, *Curr. Opin. Chem. Biol* 3:395–406; as-Obeidi et al., *Mol. Biotechnol.* 9:205–223; Qabar et al., *Farmaco* 51, 87–96. Typically this involves identification and characterization of the protein target as well as the protein ligand using X-ray crystallography and nuclear magnetic resonance technology. In the case of the factor VIIIa binding domain on factor IXa, both factors have been sequenced and cloned. Wood et al., 1984, *Nature* 312: 330–337; Vehar et al., 1984, *Nature* 312:337–342; Yoshitake et al., 1985, *Biochem.* 24:3736–3750). Additionally, the X-ray structure of factor IXa has been determined (Brandstetter et al., 1995, *Proc. Natl. Acad. Sci. USA* 92:9796–9800) and modeling studies have elucidated characteristics of the factor IXa binding site (disclosed herein in the Example 1). Using information learned from the structure of factor VIIIa and its polypeptide ligand, a pharmacophore hypothesis is developed and compounds are made and tested in an assay system. The test compound can then be evaluated by, for example, binding to factor VIIIa, e.g., by electrophoretic mobility shift assays (Igarashi et al., 1993, *Mol Cell Biol* 13, 1634–1640) or an assay system utilizing co-precipitation of the ligand and factor VIIIa. Alternatively, the compound can also be tested functionally by methods known in the art, e.g., by its ability to reduce or abolish activity of factor VIIIa in a coagulation based assay or in factor X activation assay. See, e.g., the Example 1 for such methods. As is well known, peptidomimetics and nonpeptidomimetics are often superior to analogous peptides in therapeutic applications because the mimetics are generally more resistant to digestion than peptides.

Additionally, included within the derivatives contemplated as part of the invention are the polypeptides disclosed above, wherein individual amino acids in the claimed sequence are substituted with linkers which are not amino acids but which allow other amino acids in the sequence to be spaced properly to allow binding to factor VIIIa. For example, the X$_{aa}$ of DRX$_{aa}$T can be a linker to allow the D, R, and T to align properly to bind to factor VIIIa. Use of such linkers is well known in the art and their design in this context would not require undue experimentation.

The factor VIIIa binding site on factor IXa (LVDRATCLR; SEQ ID NO:1) forms a helix in the native IXa protein (see, e.g., FIG. 7B). Short polypeptides (ca. 4–15 amino acids) comprising the essential amino acid residues of this sequence (DRX$_{aa}$T), or derivatives, are therefore most effective in binding to factor VIIIa when the polypeptide or derivative retains the native helical shape. It is known in the art that certain substitutions may be made in the sequence of short polypeptide helical sequences such as SEQ ID NO:1 to retain the helical shape and prevent undesirable secondary interactions. For example, valine (V), the native amino acid that immediately precedes the aspartic acid (D) in the native sequence can advantageously be substituted with an alanine (A). The cysteine (C) residue immediately following the threonine residue in this helix can also be substituted with an alanine (A) to prevent disulfide bridges from forming between two C residues in two polypeptides. Thus, other polypeptides or derivatives thereof within the scope of the present invention include ADRAT (SEQ ID NO:3) and DRATA (SEQ ID NO:4).

Of the invention polypeptides or derivatives that comprise DRX$_{aa}$T, the X$_{aa}$ can also be glycine (G). As is well known, a G can substitute for amino acids or spacers in many compositions since such a substitution allows increased flexibility in the compound. This is because G has hydrogen as its side chain, allowing flexibility of rotation in its Ramachandran Φ and ψ angles.

Since amino acid residues other than those in the core DRX$_{aa}$T sequence of SEQ ID NO:1 may contribute to the retention of the helical structure of the binding sites or may otherwise contribute to factor VIIIa binding, amino acids in a polypeptide which retains maximal factor VIIIa binding will be the same as, or conservative substitutions for, the amino acids at analogous positions of SEQ ID NO:1. Conservative amino acid substitutions refer to the interchangeability of residues having similar side chains. Conservatively substituted amino acids can be grouped according to the chemical properties of their side chains. For example, one grouping of amino acids includes those amino acids that have neutral and hydrophobic side chains (A, V, L, I, P, W, F, and M); another grouping is those amino acids having neutral and polar side chains (G, S, T, Y, C, N, and Q); another grouping is those amino acids having basic side chains (K, R, and H); another grouping is those amino acids having acidic side chains (D and E); another grouping is those amino acids having aliphatic side chains (G, A, V, L, and I); another grouping is those amino acids having aliphatic-hydroxyl side chains (S and T); another grouping is those amino acids having amine-containing side chains (N, Q, K, R, and H); another grouping is those amino acids having aromatic side chains (F, Y, and W); and another grouping is those amino acids having sulfur-containing side chains (C and M). Among the amino acids in SEQ ID NO:1, preferred conservative amino acid substitutions groups are: R-K; E-D, L-M, and V-I. Based on the results disclosed in the Example 1, it is believed that retention of the leucine at position 337 is particularly important in retaining optimal retention of the binding site helix (see, e.g., Table 1).

Polypeptides or derivatives comprising an amino acid sequence or derivative that prevents binding of factor IXa to factor VIIIa can be produced by a number of methods known in the art. For example, the peptide can be produced by standard synthetic procedures such as the "classical" Merrifield method of solid phase peptide synthesis or by using the FMOC strategy on a RAMPS multiple peptide synthesis system (DuPont Co., Wilmington Del.) as described in Caprino and Han, *J. Org. Chem.* 37:3404, 1972. Alternatively, the polypeptide can be produced using standard molecular biological methods. See, e.g., Fredrick M. Ausubel et al. (1995), "Short Protocols in Molecular Biology", John Wiley and Sons.

The process of identifying the factor VIIIa binding site on factor IXa is disclosed in detail herein in the Example 1. Briefly, factor IX mutants are made which alter amino acid residues being tested. The amino acid mutations can consist of amino acid replacements or deletions, or replacements or deletions of an entire domain being tested. The ability of those mutants to interfere with normal factor VIIIa binding and/or factor X activation is then determined, e.g., by determining the ability of the mutant to mediate clot formation, or, preferably, by measuring the apparent Kd (Kd, app) of binding of each mutant to VIIIa. Comparisons of the mutants with wild type factor IXa are also preferably made in both the presence and the absence of phospholipid, since regions which affect phospholipid position in relation to factor IXa would affect VIIIa binding in the presence, but not in the absence, of phospholipid, whereas mutants in a region where VIIIa binding takes place would affect the binding whether phospholipid was present or not (see Example 1).

The present invention also provides nucleic acid molecules that comprise a nucleotide sequence, or the complement thereof, which encodes a polypeptide having anti-coagulation activity. In one embodiment, the polypeptide comprises the sequence $DRX_{aa}T$, wherein $X_{aa}$ is independently any amino acid or derivative thereof. In another embodiment, the polypeptide comprises SEQ ID NO: 5 ($LVX_1X_2AT$, wherein $X_1$ is either D or Y, and $X_2$ is either R or Q), SEQ ID NO:6 (LVDRAT), SEQ ID NO:7 (LVYRAT), SEQ ID NO:8 (LVDQAT), SEQ ID NO:9 (LVDRATXLR, wherein X is any amino acid other than C), or SEQ ID NO:10 (LVDRATALR). These nucleic acid molecules can be used to produce the polypeptide, for example by culturing transgenic cells which can express the polynucleotide. To that end, the nucleic acid molecules can also encode a fusion protein comprising the polypeptide and a component, such as a histidine tag, to facilitate purification. For reasons discussed previously, the nucleotide sequence preferably encodes a polypeptide comprising SEQ ID NO:2 (DRAT) or SEQ ID NO:10 (LVDRATALR).

In other embodiments, the present invention provides methods for identifying agents having anti-coagulation activity. The method comprises determining whether a candidate agent displaces the binding of a polypeptide or derivative that binds to factor VIIIa but does not activate factor X. Suitable polypeptides or derivatives for these methods include any polypeptide or derivative which includes the sequence $DRX_{aa}T$, wherein $X_{aa}$ is independently any amino acid or derivative thereof, and which will bind to factor VIIa at the factor IXa binding site and prevent coagulation and factor X activation. In that embodiment, the preferred polypeptides or derivatives comprise the entire 9-mer binding site LVDRATCLR (SEQ ID NO:1), or the 4-mer within that sequence which contains the three crucial amino acid residues, DRAT (SEQ ID NO:2), or derivatives of those sequences. In another embodiment, the polypeptide comprises SEQ ID NO: 5 ($LVX_1X_2AT$, wherein $X_1$ is either D or Y, and $X_2$ is either R or Q), SEQ ID NO:6 (LVDRAT), SEQ ID NO:7 (LVYRAT), SEQ ID NO:8 (LVDQAT), SEQ ID NO:9 (LVDRATXLR, wherein X is any amino acid other than C), or SEQ ID NO:10 (LVDRATALR). The most preferred polypeptides or derivatives have 4–20 amino acid residues or the equivalent, but can comprise much larger sequences, including, for example, factor IXa which has been altered to eliminate its serine protease activity, e.g., by changing the active site serine to alanine.

The methods for identifying agents having anti-coagulation activity include mixing the candidate agent with factor VIIIa and the polypeptide or derivative, then determining whether less of the polypeptide or derivative binds to the factor VIIIa than the amount that binds in the absence of the polypeptide or derivative. Preferably, the candidate agent is mixed with factor VIIIa before adding the polypeptide or derivative in order to allow the candidate agent to optimally compete for factor VIIIa binding sites with the polypeptide or derivative.

The amount of binding of the polypeptide or derivative to the factor VIIIa can be determined by any of a number of methods that are well known in the art. For example, the polypeptide or derivative can be labeled with a radioactive agent or a dye such as a fluorescent dye, and unbound vs. bound polypeptide or derivative can be determined by methods such as chromatography or electrophoresis, where the chromatographic or electrophoretic conditions are selected where unbound polypeptide migrates differently than polypeptide bound to factor VIIIa. Alternatively, bound vs. unbound polypeptide or derivative can be determined by dialysis, using a membrane which allows the passage of unbound labeled polypeptide or derivative but not polypeptide or derivative bound to factor VIIIa. Another alternative method for determining polypeptide or derivative bound to factor VIIIa is by the determination of displacement of labeled polypeptide from factor VIIIa that is adsorbed to a solid phase.

In additional embodiments, the present invention provides methods of treatment to prevent thrombosis in patients in need thereof. The methods comprise administering to the patient a polypeptide or derivative which includes the sequence $DRX_{aa}T$, wherein $X_{aa}$ is any amino acid or derivative thereof, and which will bind to factor VIIIa at the factor IXa binding site and prevent coagulation and factor X activation. In that embodiment, the preferred polypeptides or derivatives comprise the entire 9-mer binding site LVDRATCLR (SEQ ID NO:1), or the 4-mer within that sequence which contains the three crucial amino acid residues, DRAT (SEQ ID NO:2), or the equivalent derivatives. In another embodiment, the polypeptide comprises SEQ ID NO: 5 ($LVX_1X_2AT$, wherein $X_1$ is either D or Y, and $X_2$ is either R or Q), SEQ ID NO:6 (LVDRAT), SEQ ID NO:7 (LVYRAT), SEQ ID NO:8 (LVDQAT), SEQ ID NO:9 (LVDRATXLR, wherein X is any amino acid other than C), or SEQ ID NO:10 (LVDRATALR). The most preferred compositions have 4–20 amino acid residues or derivatives, but can comprise much larger sequences, including, for example, factor IXa which has been altered to eliminate its serine protease activity. Antibodies that specifically bind to the above polypeptides would also be expected to prevent thrombosis through their ability to bind the same region in factor IXa. Such antibodies can be produced without undue experimentation by the skilled artisan.

It is believed that the patients in these methods can be any vertebrate animal. While the factor VIIIa binding region of factor IXa is invariant among all mammals tested (Table 2, in Example 1), it is believed that factor IXa from all vertebrates would have the same factor VIIIa binding region. However, preferred patients in these methods are mammals; most preferred patients are humans at risk for undesired thrombosis. Nonetheless, the utility of the methods with any vertebrate can be determined without undue experimentation by mixing the polypeptide or derivative with blood of the vertebrate and determining whether a clot forms as quickly as in the absence of the polypeptide. Alternatively, the utility of the method can also be assessed by evaluating binding of the polypeptide or derivative or by measuring formation of factor Xa, as described herein and/or as is well known in the art.

The polypeptides or derivatives that bind to factor VIIIa at the factor IXa binding site to prevent coagulation and factor X activation can be administered to a vertebrate by any suitable route known in the art including, for example, intravenous, subcutaneous, intramuscular, transdermal, intrathecal, or intracerebral. Administration can be either rapid as by injection or over a period of time as by slow infusion or administration of a slow release formulation.

It is contemplated that the polypeptides or derivatives of the present invention are usually employed in the form of pharmaceutical preparations. Such preparations are made in a manner well known in the pharmaceutical art. One preferred preparation utilizes a vehicle of physiological saline solution, but it is contemplated that other pharmaceutically acceptable carriers such as physiological concentrations of other non-toxic salts, five percent aqueous glucose solution, sterile water or the like may also be used. It may also be desirable that a suitable buffer be present in the composition. Such solutions can, if desired, be lyophilized and stored in a sterile ampoule ready for reconstitution by the addition of sterile water for ready injection. The primary solvent can be aqueous or alternatively non-aqueous.

The carrier can also contain other pharmaceutically-acceptable excipients for modifying or maintaining the pH, osmolarity, viscosity, clarity, color, sterility, stability, rate of dissolution, or odor of the formulation. Similarly, the carrier may contain still other pharmaceutically-acceptable excipients for modifying or maintaining release or absorption or penetration across the blood-brain barrier. Such excipients are those substances usually and customarily employed to formulate dosages for parenteral administration in either unit dosage or multi-dose form or for direct infusion by continuous or periodic infusion.

It is also contemplated that certain formulations comprising the polypeptides or derivatives are to be administered orally. Such formulations are preferably encapsulated and formulated with suitable carriers in solid dosage forms. Some examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, gelatin, syrup, methyl cellulose, methyl- and propylhydroxybenzoates, talc, magnesium, stearate, water, mineral oil, and the like. The formulations can additionally include lubricating agents, wetting agents, emulsifying and suspending agents, preserving agents, sweetening agents or flavoring agents. The compositions may be formulated so as to provide rapid, sustained, or delayed release of the active ingredients after administration to the patient by employing procedures well known in the art. The formulations can also contain substances that diminish proteolytic and nucleic acid degradation and/or substances that promote absorption such as, for example, surface active agents.

The polypeptide or derivative is administered to vertebrates in an amount effective to decrease thrombosis within the vertebrate. The specific dose is calculated according to the approximate body weight or body surface area of the patient or the volume of body space to be occupied. The dose will also be calculated dependent upon the particular route of administration selected. Further refinement of the calculations necessary to determine the appropriate dosage for treatment is routinely made by those of ordinary skill in the art. Such calculations can be made without undue experimentation by one skilled in the art in light of the activity disclosed herein in thrombosis assays. Exact dosages are determined in conjunction with standard dose-response studies. It will be understood that the amount of the composition actually administered will be determined by a practitioner, in the light of the relevant circumstances including the condition or conditions to be treated, the choice of composition to be administered, the age, weight, and response of the individual patient, the severity of the patient's symptoms, and the chosen route of administration. Dose administration can be repeated depending upon the pharmacokinetic parameters of the dosage formulation and the route of administration used.

In other embodiments of the invention, methods of treatment are provided for preventing thrombosis in a patient. These methods comprise selecting an agent having anti-coagulation activity, wherein the selecting comprises testing the agent for activity in displacing the binding of factor IXa from factor VIIIa without activating factor X, and administering the agent to the patient. The selecting step in this embodiment is identical to the method of identifying an agent having anti-coagulation activity previously disclosed, and can be performed in the same manner. Additionally, the treatment step in this embodiment can be performed as with the polypeptide or derivative treatment step disclosed above.

In additional embodiments of the invention, methods are provided for preventing coagulation in a blood sample. The methods comprise mixing a freshly drawn blood sample with a polypeptide or derivative which includes the sequence $DRX_{aa}T$ or derivatives, wherein $X_{aa}$ is any amino acid or derivative thereof, and which will bind to factor VIIIa at the factor IXa binding site and prevent coagulation and factor X activation. In that embodiment, the preferred polypeptides or derivatives comprise the entire 9-mer binding site LVDRATCLR (SEQ ID NO:1), or the 4-mer within that sequence which contains the three crucial amino acid residues, DRAT (SEQ ID NO:2), or derivatives of these sequences. In another embodiment, the polypeptide comprises SEQ ID NO: 5 ($LVX_1X_2AT$, wherein $X_1$ is either D or Y, and $X_2$ is either R or Q), SEQ ID NO:6 (LVDRAT), SEQ ID NO:7 (LVYRAT), SEQ ID NO:8 (LVDQAT), SEQ ID NO:9 (LVDRATXLR, wherein X is any amino acid other than C), or SEQ ID NO:10 (LVDRATALR). The most preferred compositions have 4–20 amino acid residues or derivatives, but can comprise much larger sequences, including, for example, factor IXa which has been altered to eliminate its serine protease activity. An antibody that specifically binds to these sequences would also be expected to prevent coagulation in a blood sample. Such antibodies can be produced without undue experimentation by a skilled artisan.

In these methods, the polypeptide or derivative can be added to the blood sample as a liquid or dried preparation. Alternatively, the polypeptide can be present in the container that receives the blood sample (for example a vacutainer), in order for the blood sample to be exposed to the polypeptide when the sample enters the container. The quantity of the polypeptide or derivative added to the container can be determined without undue experimentation, merely by determining the quantity of the polypeptide or derivative necessary to prevent coagulation of the quantity of blood which is to be drawn in the sample.

Other embodiments of the invention include the provision of methods for detecting factor VIIIa in a sample. These methods comprise contacting the sample with a polypeptide or derivative which will bind to factor VIIIa at the factor IXa binding site and prevent coagulation and factor X activation, then determining whether the polypeptide or derivative has bound factor VIIIa. Preferably, the polypeptide or derivative comprises a covalently attached detectable moiety, as previously disclosed. The polypeptide comprises the sequence $DRX_{aa}T$ or derivative, wherein $X_{aa}$ is any amino acid or derivative thereof. In that embodiment, the preferred polypeptides comprise the entire 9-mer binding site LVDRATCLR (SEQ ID NO:1), or the 4-mer within that sequence which contains the three crucial amino acid residues, DRAT (SEQ ID NO:2), or derivatives of these sequences. In another embodiment, the polypeptide comprises SEQ ID NO: 5 ($LVX_1X_2AT$, wherein $X_1$ is either D or Y, and $X_2$ is either R or Q), SEQ ID NO:6 (LVDRAT), SEQ ID NO:7 (LVYRAT), SEQ ID NO:8 (LVDQAT), SEQ ID NO:9 (LVDRATXLR, wherein X is any amino acid other than C), or SEQ ID NO:10 (LVDRATALR). The most preferred polypeptides have 4–20 amino acid residues, but can comprise much larger sequences, including, for example, factor IXa which has been altered to eliminate its serine protease activity.

The determination of whether the polypeptide or derivative has bound factor VIIIa can be accomplished by any method known in the art, for example by methods such as chromatography or electrophoresis, where the chromatography or electrophoretic conditions are selected such that labeled polypeptide or derivative that is bound to factor VIIIa will have a different migration rate than unbound polypeptide, or dialysis, using a membrane that allows passage of unbound, labeled polypeptide but not labeled polypeptide or derivative bound to factor VIIIa. Alternatively, activation of factor X can be evaluated in the presence or absence of the polypeptide or derivative, as previously discussed. See also Example 1.

INDUSTRIAL APPLICATION

The compositions and methods of the present invention provide novel treatments to prevent thrombosis, methods for preventing coagulation in blood samples, and methods for identifying agents that have anti-coagulation activity.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

The procedures disclosed herein which involve the molecular manipulation of nucleic acids are known to those skilled in the art. See generally Fredrick M. Ausubel et al. (1995), "Short Protocols in Molecular Biology", John Wiley and Sons, and Joseph Sambrook et al. (1989), "Molecular Cloning, A Laboratory Manual", second ed., Cold Spring Harbor Laboratory Press, which are both incorporated by reference.

EXAMPLE 1

This example describes the determination and characterization of the factor VIIIa binding region of factor IXa.

The following reagents were used. Benzoyl-Ile-Glu-Gly-Arg-p-nitroanilide (SEQ ID NO: 17) (S-2222) was purchased from Helena Laboratories. Dansyl-Glu-Gly-Arg-chloromethyl ketone (DEGR-ck) was obtained from Calbiochem. Phosphatidylcholine, phosphatidylserine, recombinant hirudin, and fatty acid free bovine serum albumin (BSA) were obtained from Sigma Chemical Co. Factor IX and factor VIII deficient plasmas were purchased from George King Biomedicals and aPTT reagent was obtained from Diagnostica Stago. Normal human plasma factor IX ($IX_{NP}$) and factor X were isolated as described in Bajaj and Birktoft, 1993, *Methods Enzymol.* 222, 96–128, and factor Xa was prepared as described in Bajaj et al., 1981, *Prep. Biochem.* 11, 397–412. Purified human factor XIa, protein C, activated protein C, and α-thrombin (IIa) were purchased from Enzyme Research Laboratories (South Bend, Ind.). Recombinant human tissue factor of aa 1–243 containing the transmembrane domain was generously provided by Genentech Inc. (South San Francisco, Calif.) and reconstituted as described in Sabharwal et al., 1995, *J. Biol. Chem.* 270, 15523–15530. Phosphatidylcholine-phosphatidylserine vesicles (75% phosphatidylcholine, 25% phosphatidylserine) were prepared by the method of Husten et al., 1987, *J. Biol. Chem.* 262, 12953–12966 as outlined in Sabharwal et al (Id.). Recombinant human factor VIIa was a generous gift of Novo-Nordisk (Copenhagen). Purified human factor VIII was obtained from Dr. Leon Hoyer (American Red Cross, Rockville, Md.). The preparation was free of all other coagulation factors and contained human albumin as a stabilizing agent. Purification of a mouse monoclonal antibody (mAb) that inhibits the interaction of factor IXa with factor VIIIa was as described in Bajaj et al., 1985, *J. Biol. Chem.* 260:11574–11580.

To evaluate the role of various factor IXa sites in factor VIIIa binding, recombinant factor IX proteins with mutations at the sites to be tested were generated as follows. The pRc/CMV vector (Invitrogen) was used for expression of wild-type and each mutant factor IX. In each case Hind III and Xba I sites in the multiple cloning sites of the vector were used for ligation of the DNA. Construction of the wild-type factor IX ($IX_{WT}$) and that of $IX_{PCEGF1}$, in which residues 52–85 in the EGF1 domain of $IX_{WT}$ have been replaced by the residues 51–92 from the corresponding domain of protein C, have been described (Zhong and Bajaj, 1993, *Biotechniques* 15, 874–878). Point mutations in the helix-330 [162 by chymotrypsin numbering] of the protease domain of factor IX were introduced using the fragment elongation method of Nelson and Long, 1989, *Anal. Biochem.* 180, 147–181 as described previously for $IX_{Q50P}$ (Zhong et al., supra). In each case the mutant primer was based upon the factor IX gene sequence (Yoshitake et al., supra) and corresponded to six codons (18 bases) with a mutant base at the desired position involving the third codon. The base substitution for each point mutant was: L330I (CTT→ATT), V331A (GTT→GCT), D332Y (GAC→TAC), R333L (CGA→CTA), R333Q (CGA→CAA), T335A (ACA→GCA), L337I (CTT→ATT)

and R338Q (CGA→CAA). Factor IX$_{helixVII}$, in which 330–338 residues of factor IX [chymotrypsin 162–170] were replaced by the corresponding residues of factor VII, was constructed using a 63-base primer. The first 18 bases of this primer corresponded to factor IX gene sequence coding for residues 324 to 329 [chymotrypsin 156 to 161] followed by 27 bases from the factor VII gene sequence (O'Hara et al., 1987, *Proc. Natl. Acad. Sci. USA* 84, 5158–5162) coding for the residues equivalent to 330–338 [chymotrypsin 162 to 170], and the final 18 bases corresponded to the factor IX gene sequence coding for residues 339 to 344 [171 to 177]. The PCR was performed in the same fashion as described earlier for point mutants (Zhong et al., supra; Nelson and Long, supra). All inserts were sequenced (Sanger et al., 1977, *Proc. Natl. Acad. Sci. USA* 74, 5463–5467) to confirm the mutations and to rule out any PCR errors. Expression of each factor IX recombinant protein and its purification was achieved exactly as described in Zhong et al., supra.

SDS-polyacrylamide gel electrophoretic analysis of factor IX proteins (Laemmli, 1970, *Nature (London)* 227, 680–685), using a 12% polyacrylamide concentration and Coomassie Brilliant Blue staining, is shown in FIG. 1A. Each protein appeared homogenous in this system. γ-carboxyglutamic acid concentration of these proteins was also determined by Commonwealth Biotechnologies, Inc., Richmond, Va. Automated Edman degradation of each factor IX protein (~0.5 nmol) was performed using an Applied Biosystems gas phase sequencer. γ-carboxyglutamic acid analysis of each sample was performed by alkaline hydrolysis followed by HPLC analysis. The amount of γ-carboxyglutamic acid was quantitated based upon the 46 residues of Asp and Asn present per mol of factor IX. Plasma factor IX and each recombinant protein had 11.5 to 12.5 γ-carboxyglutamic acid residues per mol. The N-terminal sequence of each protein was also determined. All recombinant proteins revealed a major and a minor N-terminal sequence. The major sequence in each case was Tyr-Asn-Ser-Gly-Lys (SEQ ID NO: 11) and the minor sequence in each case was Thr-Val-Phe. The major sequence corresponds to the sequence of mature protein in plasma, and the minor sequence corresponds to the protein in which the prosequence has not been cleaved (Yoshitake et al., supra). The minor sequence was not detected in plasma factor IX and it amounted to less than 5% in each recombinant protein. The relative coagulant activity of each protein was: IX$_{NP}$, 100% (180±10 units/mg); IX$_{WT}$, ~90%; IX$_{L330I}$, ~8%; IX$_{V331A}$, ~6%; IX$_{D332Y}$, ~2%; IX$_{R333L}$, 0.3%; IX$_{R333Q}$, ~0.5%; IX$_{T335A}$, ~40%; IX$_{L337I}$, ~1%; IX$_{R338Q}$, ~65%; and IX$_{helixVII}$, not measurable.

The ability of the IX mutant proteins to bind to a mAb (Bajaj et al., 1985, supra) which interferes with the interaction of IXa and VIIIa was studied using a coagulant based assay as described in Usharani et al., 1985, *J. Clin. Invest.* 75, 76–83. For mutants that possessed ≦8% coagulant activity, a competition based assay in which the mutant protein competed with the normal IX in binding to the mAb was used (Id.). Each mutant protein bound to the mAb with an equal affinity (Kd~15±8 nM).

Figure 1B:
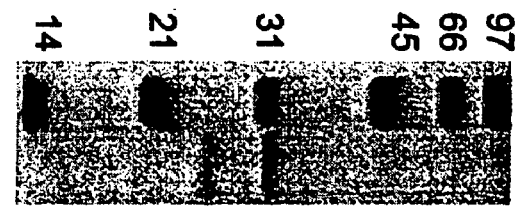
FIG. 1B depicts the same analysis as in FIG. 1A, after the factor IX protein was activated for 90 min at 37° C., where "IX" indicates the migration position of a single chain IX of residues 1–415, H$_\alpha$ is the migration of the heavy chain of factor IX activation intermediate comprised of residues 146–415, H$_\beta$ is the migration of the heavy chain of factor IXa comprised of residues 181–415, L is the migration of the light chain of factor IXa comprised of residues 1–145, and the two digit numbers indicate the migration of molecular weight markers. Activation peptide (AP) which is comprised of residues 146–180, stains poorly and was not observed on these gels.
Figure 1B:
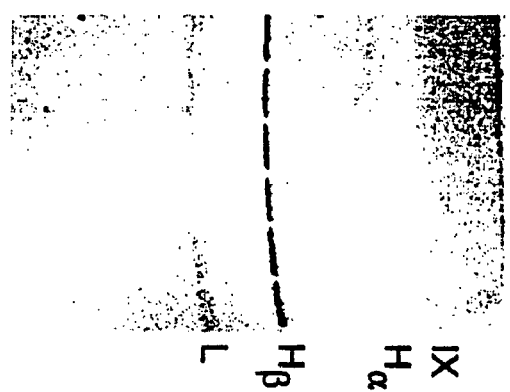

The rates of activation of the protease domain factor IX mutants by VIIa/TF and by Factor XIa/Ca$^{2+}$ was also determined, under conditions described in Mathur et al., 1997, supra, either by VIIa/TF/Ca$^{2+}$ or by factor XIa/Ca$^{2+}$. The rates of the mutants were similar to that of IX$_{NP}$ as analyzed by SDS gel electrophoresis. The 90 min activation sample of IX$_{WT}$ and each mutant is shown in FIG. 1B. As compared to IXa$_{NP}$, coagulant activity of XIa-activated IXa$_{WT}$ was ~95%, of IXa$_{L330I}$ was ~7%, of IXa$_{331A}$ was ~6%, of IXa$_{D332Y}$ was ~2%, of IXa$_{333L}$ was ~0.4%, of IXa$_{R333Q}$ was ~0.6%, of IXa$_{T335A}$ was ~35%, of IXa$_{L337I}$ was ~0.8%, of IXa$_{R338Q}$ was ~80%, and of IXa$_{helixVII}$ was not measurable.

The ability of each activated mutant to activate factor X in the presence and absence of phospholipid and factor VIIIa was determined as follows. The activation was carried out at 37° C. in a 50 µl reaction volume, in TBS/BSA pH 7.4, for various time periods. At the end of the incubation time period, each reaction mixture received 1 µl of 0.5 M EDTA to stop further generation of factor Xa. A 40 µL aliquot was then added to 0.1 ml quartz cuvette containing S-2222 in 75 µL of TBS/BSA, pH 7.4. The final concentration of S-2222 was 100 µM. The p-nitroaniline release was measured continuously (ΔA$_{405}$/min) for up to 20 min (Sabharwal et al., 1995 supra; Sabharwal et al., 1997, supra). Factor Xa generated was calculated from a standard curve constructed using factor Xa prepared from insolubilized Russell's viper venom.

Factor X activation measurements were made under four experimental regimes. In one, Ca$^{2+}$ and phospholipid were present. In this system activation was carried out for 5–15 minutes and the concentration of each IXa protein was 20 nM, phospholipid was 25 µM, and factor X was 100 nM. In the second regime, Ca$^{2+}$, phospholipid and factor VIIIa were present. Activation was carried out here for 15–120 sec and the concentration of each IXa protein was 0.5 nM, phospholipid was 10 µM, VIIIa was 0.07 nM and factor X was 15 nM. In the third regime, only Ca$^{2+}$ was present. Here, activation was carried out for 2–20 min and concentration of each IXa protein was 400 nM and factor X was 1 µM. Finally, in the fourth regime, Ca$^{2+}$ and VIIIa were present. Here, activation was carried out for 15–120 sec and the concentration of each IXa protein was 2 µM, VIIIa was 14 nM, and factor X was 400 nM.

In all of the above factor X activation experiments, the incubation times chosen were those in which the factor Xa generated was always less than 10 nM. This precautionary measure was taken to prevent activation of factor X by the generated factor Xa (see, e.g., Link. and Castellino, 1982, *Arch Biochem. Biophys.* 215, 215–221). Further, in those incubation mixtures which contained factor VIIa, control experiments were also performed in which factor VIIIa was omitted. The rates of factor X activation in those control experiments were <10% of the experimental values in the presence of factor VIIIa and were subtracted prior to analysis of the data. For reactions done in the presence of Ca$^{2+}$ and phospholipid, optimal concentrations of phospholipid were determined. Rates of factor X activation versus phospholipid showed a bell shaped curve with a broad optima between 20–40 µM phospholipid. The rate increased linearly from 0–20 µM and after 40 µM it showed a gradual decrease. Therefore, phospholipid concentration in the absence of factor VIIIa was fixed at 25 µM. In the presence of factor VIIIa, 10 µM phospholipid was used based upon previous observations (Mathur et al., 1997, supra; van Dieijen et al., 1981, *J. Biol. Chem.* 256, 3433–3442). The concentrations of factor X selected for each set of reaction conditions are those which are below or at the Km values (van Dieijen et al., supra; Fay and Koshibu, 1998, *J Biol. Chem.* 273, 19049–19054). In this region of the Michaelis-Menton curve, the rate of formation of factor Xa is proportional to the substrate factor X and therefore to the affinity of the factor IXa enzyme for factor X.

Figure 2A:
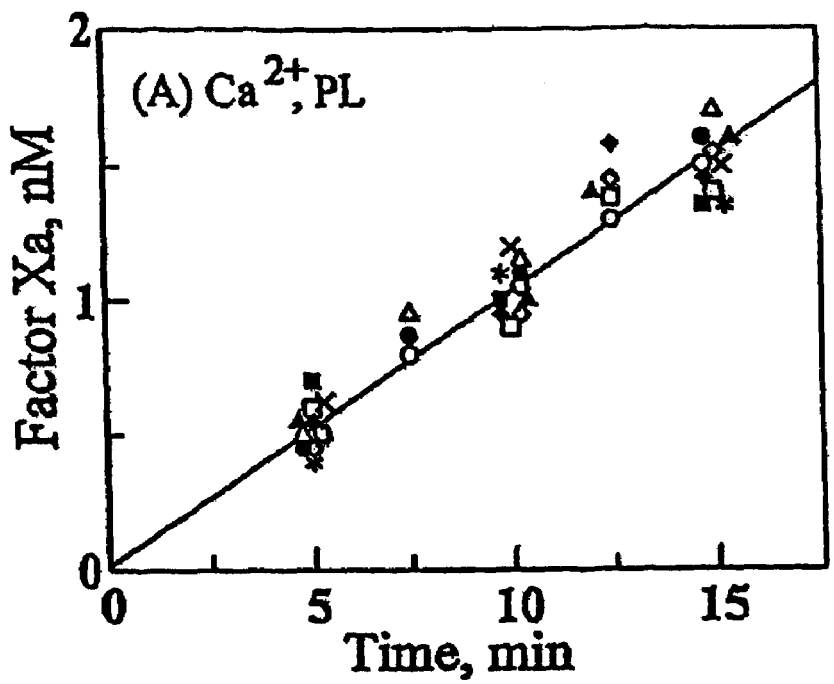
FIG. 2A depicts the time course of factor X activation by each protease domain Ixa mutant in a system containing Ca$^{2+}$ and phospholipid (PL), in an activation mixture without VIIIa, where Xa generated was measured by S-2222 hydrolysis, and where the Factor IXa proteins are: WT (○), L330I (*), V331A (■), D332Y (Δ), R333L (▼), R333Q (□), T335A (◇), L337I (♦), R338Q (●), and IXa$_{helixVII}$ (X).

The data obtained in the presence of Ca$^{2+}$ and phospholipid are shown in FIG. 2A. One should note that the concentration of factor X used in this system was 100 nM, which is slightly less than the Km value under these conditions. In this system, factor IXa$_{WT}$ and each mutant including IXa$_{helixVII}$ activated factor X at similar rates. The rate of factor Xa generation in each case was 0.1 nM/min, which is very close to an expected rate (0.12 nM/min) at an enzyme concentration of 20 nM used in this system. This indicates that, in the IXa-Ca$^{2+}$-phospholipid system, each mutant interacts with factor X normally and that the active site of each mutant is not impaired.

Figure 2B:
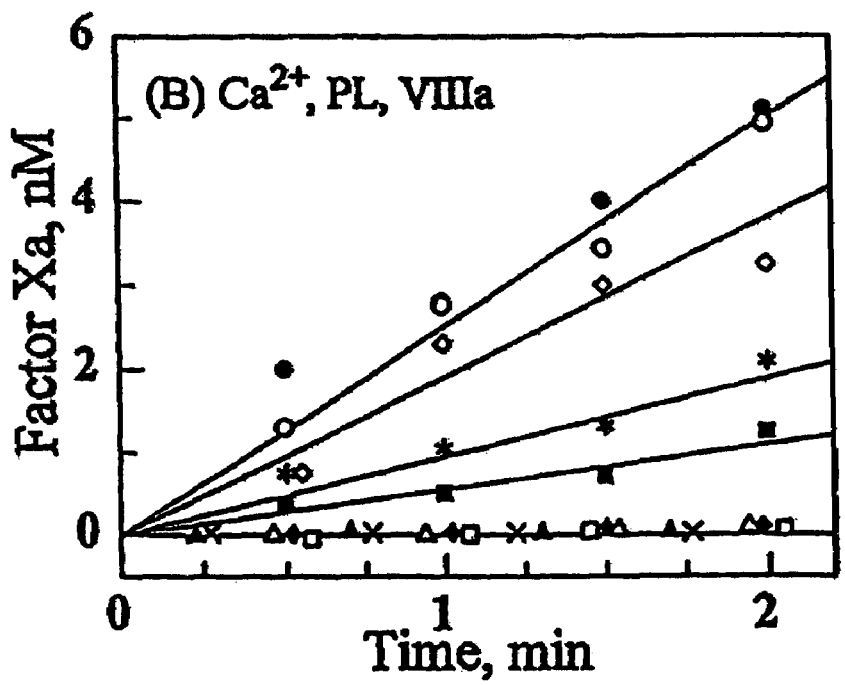
FIG. 2B depicts the time course of the factor VIIIa mediated potentiation of factor X activation by each protease domain IXa mutant in a system containing Ca$^{2+}$ and phospholipid (PL), in an activation mixture with VIIIa, wherein the symbols for the IXa proteins are the same as in FIG. 2A.

Next, the activation of factor X in a complete intrinsic Tenase system (IXa, Ca$^{2+}$, phospholipid, VIIIa) was studied. When a limiting concentration of factor VIIIa (70 pM) at 0.5 nM IXa and 15 nM factor X was employed, the rate of activation by each IXa mutant with the exception of IXa$_{R338Q}$ was significantly reduced. These data are provided in FIG. 2B and summarized in Table 1. Considering an EC$_{50}$ (functional Kd of IXa:VIIIa interaction) value of 1.2 nM (Mathur et al., 1997, supra), a kcat value of 300/min and a Km of 25 nM under these conditions (Fay and Koshibu, supra), an expected rate of factor X activation would be 2.3 nM/min; this rate is close to the rate of 2.6±0.2 nM/min observed here. Under these conditions, the rate of factor X activation by IXa$_{L330I}$ was ~0.95 nM/min, by IXa$_{V331A}$ was ~0.55 nM/min, and by IXa$_{T335A}$ was ~1.9 nM/min. For IXa$_{R338Q}$, it was the same as IXa$_{WT}$ and for other mutants (see Table 1) it could not be measured. However, when factor VIIIa concentration was increased from 70 pM to 14 nM, the following rates of factor X activation were obtained—IXa$_{D332Y}$ ~4.1 nM/min, IXa$_{P333L}$ ~2.7 nM/min, IXa$_{R333Q}$ ~2.4 nM/min, and IXa$_{L337I}$ ~3.2 nM/min; for IXa$_{helixVII}$ it was still not measurable. Note that a calculated rate for IXa$_{WT}$ (or IXa$_{NP}$) at 14 nM VIIIa would be 0.85 nM of Xa generated per sec. Thus each of our protease domain mutants except IXa$_{R338Q}$ is impaired in its interaction with VIIIa in the IXa-Ca$^{2+}$-phospholipid-VIIIa system.

Figure 3A:
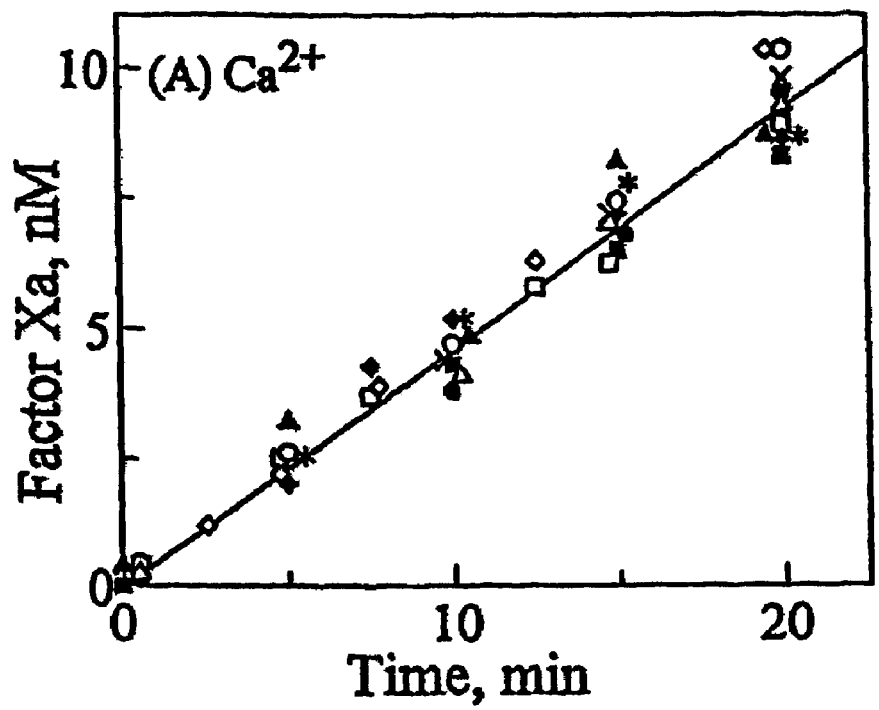
FIG. 3A depicts the time course of factor X activation under conditions as in FIG. 2A, but without phospholipid, wherein the symbols for the IXa proteins are the same as in FIG. 2A.
Figure 3B:
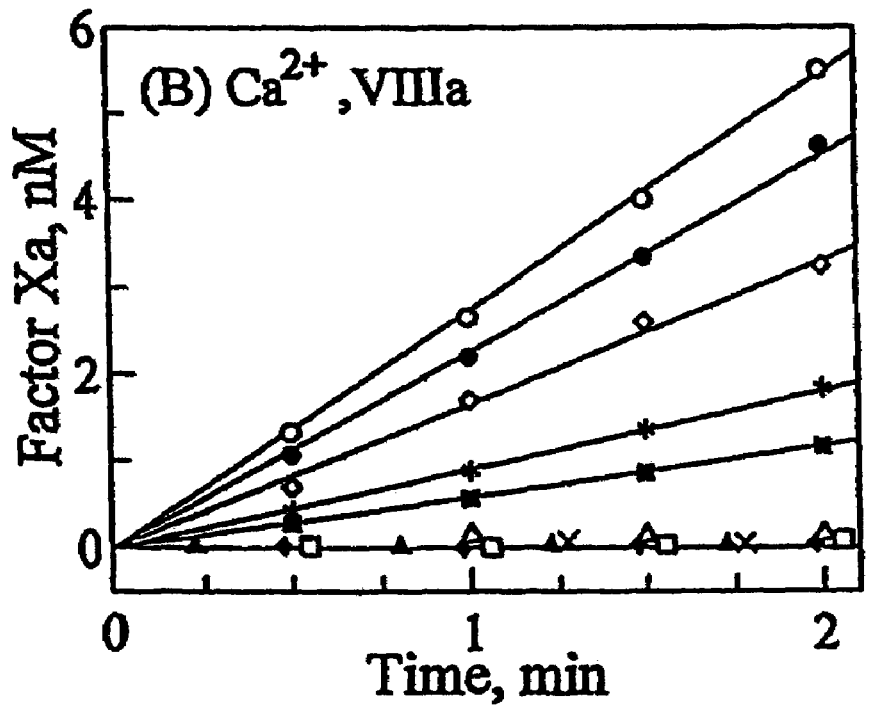
FIG. 3B depicts the time course of factor X activation under conditions as in FIG. 3A, but including Factor VIIIa, wherein the symbols for the IXa proteins are the same as in FIG. 2A.

Mutations in factor IXa can affect VIIIa binding by at least two mechanisms. One, by perturbation of factor IXa binding site for factor VIIIa and, two, by altering the spacing above the phospholipid surface of the IXa interactive site. To distinguish between these two possibilities, the effect of VIIIa on the potentiation of factor X activation in the absence of phospholipid was evaluated. For these studies, the rates of factor X activation by the IXa mutants was measured in the presence of Ca$^{2+}$ only. These data are presented in FIG. 3A. As predicted from the Ca$^{2+}$/phospholipid system, each IXa mutant in the presence of Ca$^{2+}$ only activated factor X at a rate (0.46±0.05 nM/min) comparable to IXa$_{WT}$. However, as was the case with the Ca$^{2+}$/phospholipid/VIIIa system, the IXa mutants also activated factor X in the Ca$^{2+}$/VIIIa system at rates that were slower than those obtained with IXa$_{WT}$ (or IXa$_{NP}$). These data are presented in FIG. 3B and summarized in Table 1. Considering a kcat value of 1.1/min, a km of 380 nM and an EC$_{50}$ (functional Kd of IXa:VIIIa interaction) value of 2.2 µM (16) at 400 nM factor X concentration used in our system, the expected rate of Xa formation using 14 nM VIIIa and 2 µM IXa would be 3.3 nM/min. The experimental rate obtained with IXa$_{WT}$ (or IXa$_{NP}$) was ~2.75 nM/min, a value close to the expected value. The rate of activation by IXa$_{L330I}$ was ~0.94 nM/min, by IXa$_{V331A}$ was ~0.54 nM/min, by IXa$_{T335A}$ was ~1.83 nM/min and by IXa$_{R338Q}$ was ~2.22 nM/min. Under these conditions, i.e., in the presence of limiting concentrations of VIIa, the rates of factor X activation by other mutants could not be measured. Cumulatively, these data indicate that the mutations in the helix-330 [chymotrypsin 162] residues lead to an impaired interaction of IXa with VIIIa which does not appear to be due to spatial misalignment of the IXa contact site above the phospholipid surface. These data also indicate that IXa residue R338 [170] does not play a significant role in binding to factor X or to factor VIIa.

Apparent Kds of factor VIIIa binding to various active site-blocked factor IXa proteins were determined from inhibition experiments as detailed in Mathur et al., 1997, supra. Briefly, reaction mixtures (50 µl) in the presence of phospholipid contained 0.2 nM factor IXa$_{WT}$, 0.48 µM factor X, 0.07 nM factor VIIIa, 5 mM Ca$^{2+}$, 10 µM phospholipid and varying concentrations of DEGR-IXa proteins. Reaction mixtures in the absence of phospholipid contained 0.1 nM factor IXa$_{WT}$, 2 µM factor X, 14 nM factor VIIIa, 5 mM Ca$^{2+}$, and varying concentrations of DEGR-IXa proteins. Reactions were carried out for 2 min and the rates of factor X activation were measured as outlined above.

Various DEGR-ck-inhibited factor IXa proteins were prepared for these experiments as follows. IX$_{NP}$, IX$_{WT}$, and each mutant factor IX at 200 µg/ml was activated by factor XIa (2 µg/ml) for 90 min. in TBS, pH 7.4 (0.05 M Tris, 0.15 M NaCl, pH 7.4) containing 5 mM Ca$^{2+}$. SDS-gel electrophoretic analysis revealed full activation to factor IXa without further degradation. DEGR-IXa$_{NP}$, DEGR-IXa$_{WT}$, and various DEGR-IXa mutant proteins were prepared as described in Mathur et al., 1997, supra, and free DEGR-ck was removed as described in Sabharwal et al., 1995, supra and Krishnaswamy, 1992, *J. Biol. Chem.* 267, 23696–23706. DEGR-activated protein C was prepared similarly.

Under these experimental conditions, both in the presence and absence of phospholipid, factor IXa$_{WT}$ concentrations are below the EC$_{50}$ values at the factor X concentrations used. Further, in each case <10% of factor IXa is bound to factor VIIIa in the absence of the competitor and no measurable rates of activation of factor X were observed under these conditions in the absence of added factor VIIIa. For obtaining IC$_{50}$ values (concentration of DEGR-IXa yielding 50% inhibition), the data were fitted to the IC$_{50-4}$ parameter logistic equation of Halfman, 1991, *Meth. Enzymol.* 74, 481–508 given below:

$$y = \frac{a}{1 + (x/IC_{50})^s} + \text{background} \qquad (\text{Eq. 1})$$

where y is the rate of Xa formation in the presence of a given concentration of DEGR-IXa protein represented by x, a is the maximum rate of Xa formation in the absence of DEGR-IXa, and s is the slope factor. Each point was weighted equally and the data were fitted to Equation 1 using the nonlinear regression analysis program obtained from Erithacus Software (GraFit). The values of the slope factors were 0.9±0.1 in all experiments indicating competition for a single binding site. The background value represented <5% of the maximum rate of Xa formation in the absence of DEGR-IXa. To obtain the Kd,app values for the interaction of DEGR-IXa proteins with factor VIIIa, the following equation was used, as described by Cheng and Prusoff, 1973, *Biochem. Pharmacol.* 22, 3099–3108 and further discussed by Craig, 1993, *Trends Pharmacol. Sci.* 6, 68–71.

$$Kd, app = \frac{IC_{50}}{1 + (A/EC_{50})} \qquad (\text{Eq. 2})$$

where A is the concentration of IXa$_{WT}$ and EC$_{50}$ is the concentration of factor IXa$_{WT}$ that gives a 50% maximum response in the absence of the competitor at a specified concentration of factor X used in the experiment.

Figure 4A:
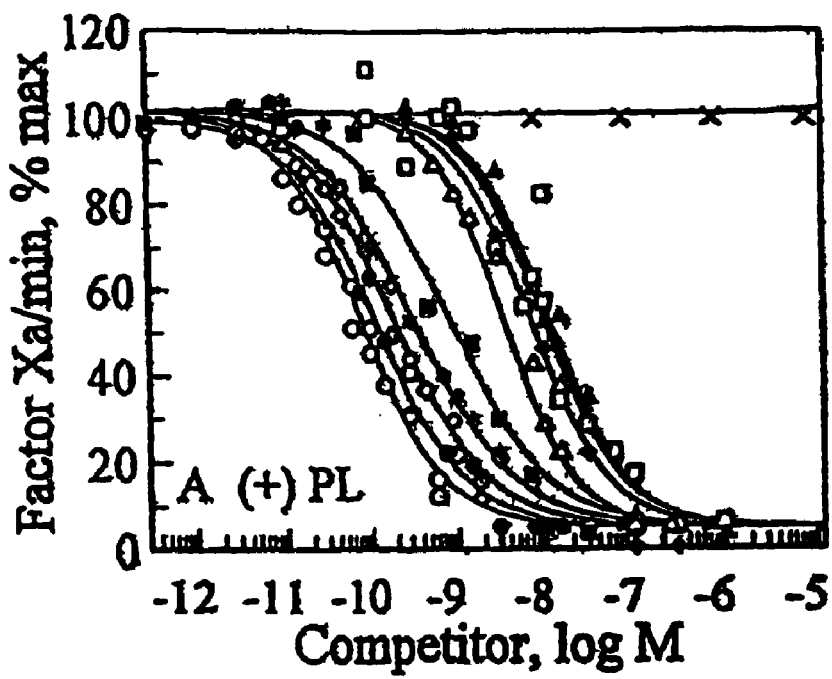
FIG. 4A depicts the inhibition of factor Xa generation by the active site-blocked protease domain IXa mutants in the presence of factor VIIIa and phospholipid, wherein the symbols for the IXa proteins are the same as in FIG. 2A.
Figure 4B:
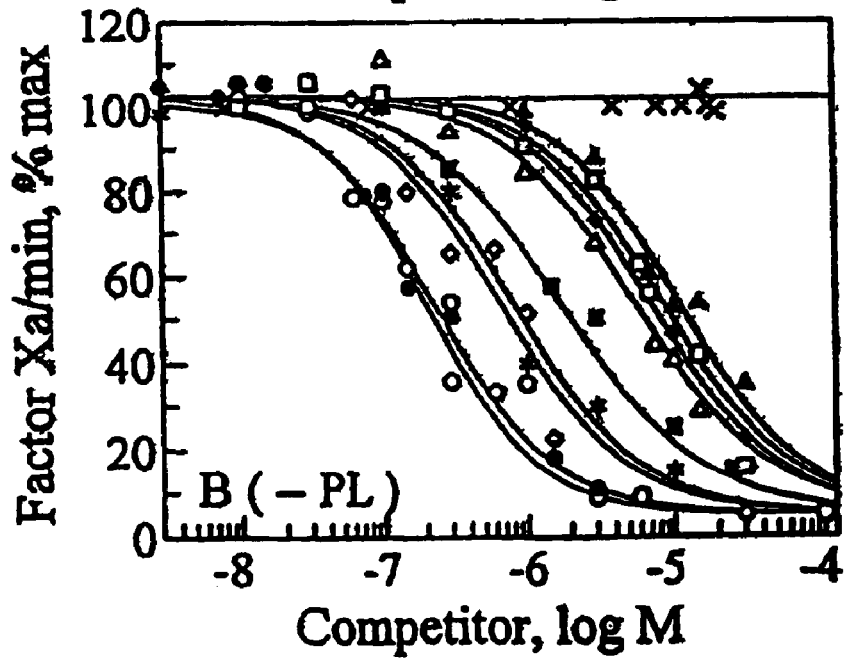
FIG. 4B depicts the inhibition of factor Xa generation by the active site-blocked protease domain IXa mutants in the presence of factor VIIIa but without phospholipid, wherein the symbols for the IXa proteins are the same as in FIG. 2A.

The steady-state inhibition curves (Bylund and Toews, 1993, *Am. J. Physiol.* 265, L421-L42) obtained from these experiments are shown in FIG. 4, in the presence (FIG. 4A) and absence (FIG. 4B) of phospholipid. The Kd,app values for the interaction of active-site blocked mutants with factor VIIIa are listed in Table 1. The binding of factor VIIIa to each active-site blocked mutant (except for $IXa_{R338Q}$) was considerably weaker both in the presence and absence of phospholipid. Compared with $DEGR-IXa_{WT}$, L330I and T335A mutants had similarly (~4-fold and ~2.5-fold, respectively) reduced affinity for factor VIIIa in the presence or absence of phospholipid. However, other mutants (Table 1) had 2- to 3-fold further reduction in affinity in the presence of phospholipid versus in its absence. The fold-reduction in affinity for these mutants in the presence and absence of phospholipid, respectively, were: V331A, 11 and 7; D332Y, 52 and 27; R333L, 149 and 67; R333Q, 130 and 41; and L337I, 91 and 32. Conceivably, in these mutants, in addition to the perturbation of factor VIIIa binding site, a further reduced affinity in the presence of phospholipid could in part be due to the misalignment of the factor VIIIa contact site. It is noteworthy that $IXa_{VIIhelix}$ mutant failed to bind to factor VIIIa at concentrations ~140,000-fold greater than the Kd,app for $IXa_{WT}$ in the presence of phospholipid and at concentrations ~150-fold greater than the Kd,app in the absence of phospholipid. Thus both the kinetic and the binding data provide strong evidence that the helix-330 in the protease domain of factor IXa provides a critical binding site for factor VIIIa.

Although compelling evidence is provided above that the IXa helix-330 constitutes a critical binding site for factor VIIIa, evidence in the involvement of the EGF1 domain in this binding has also been previously presented (Lenting et al., supra; Rees et al., 1988, *EMBO J.* 7, 2053–2061; Hughes et al., 1993, *J. Biol.Chem.* 268, 17727–17733). Notably, essentially all of the studies related to the EGF1 domain have been conducted in the presence of phospholipid. Thus one cannot differentiate whether the EGF1 domain is directly involved in binding to factor VIIIa or whether alterations in this region result in a misalignment above the phospholipid surface of the region(s) in the protease domain which is the direct contact site in interacting with factor VIIIa. To address this, the two EGF1 mutants previously generated (Zhong et al., 1994, supra) were utilized in the presence or absence of phospholipid in binding studies. The two mutants employed for these studies were factor $IX_{Q50P}$ that lacks the EGF1 domain $Ca^{2+}$ binding site, and $IX_{PCEGF1}$, in which the EGF1 domain of factor IX has been replaced by that of protein C. Both mutants had the same N-terminal sequence and the γ-carboxyglutamic acid content as normal IX and could be readily activated to IXa-like molecules by factor Xla. As discussed above, these mutants also bind to the mAb (that interferes with the IXa:VIIIa interaction) with the same affinity (kd ~15 nM) as normal IX.

Figure 5A:
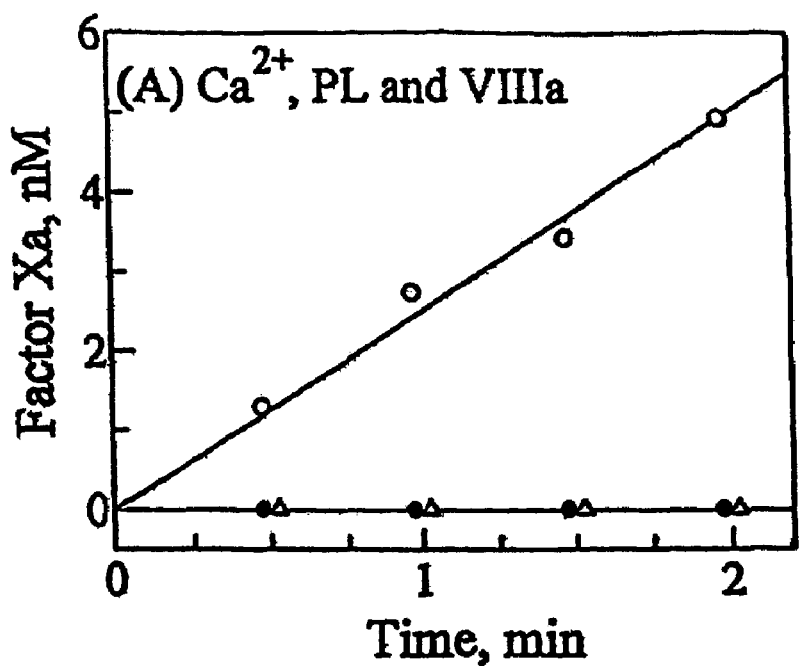
FIG. 5A depicts factor VIIIa mediated potentiation of factor X activation by the EGF1 domain IXa mutants in the presence of phospholipid, where the factor IXa proteins are WT (○), Q50P (●), and IX$_{PCEGF1}$ (Δ).
Figure 5B:
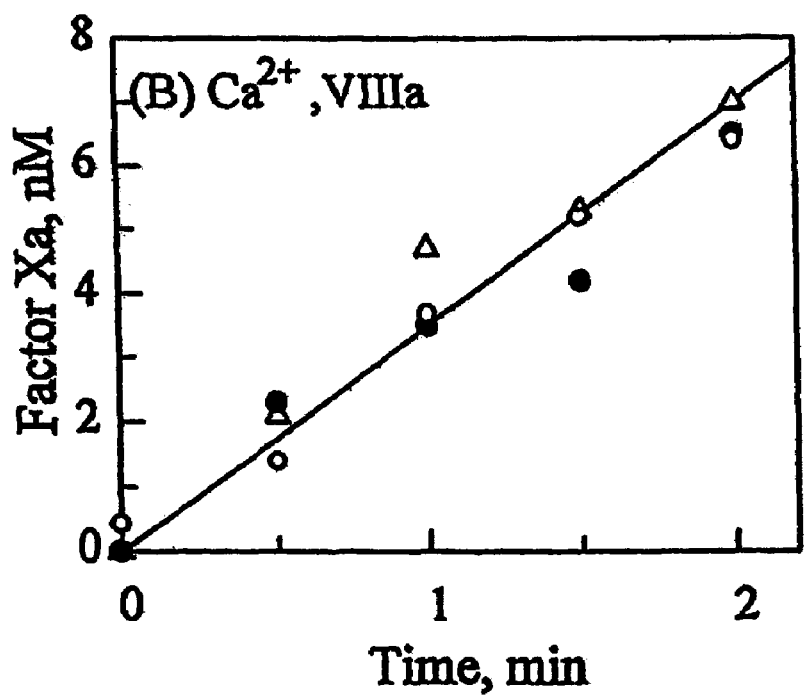
FIG. 5B depicts factor VIIIa mediated potentiation of factor X activation by the EGF1 domain IXa mutants in the absence of phospholipid, where the symbols for the IXa proteins are the same as in FIG. 5A.
Figure 6A:
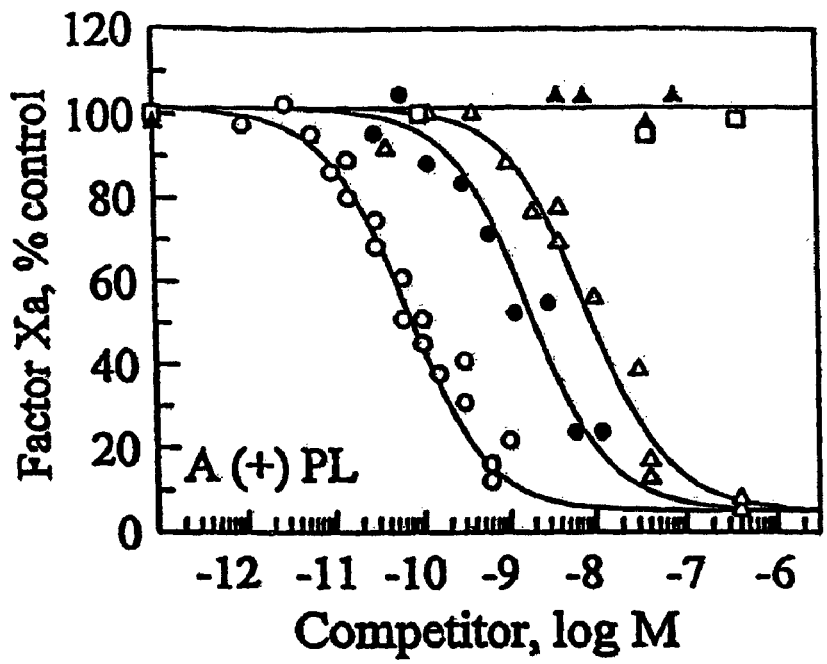
FIG. 6A depicts the inhibition of factor Xa generation by the active-site blocked (DEGR) EGF1 domain IXa mutants in the presence of phospholipid, where the DEGR-IXa proteins are WT (○); Q50P (●); and IX$_{PCEGF1}$ (Δ) and control proteins are protein C zymogen (□) and DEGR-activated protein C (APC) (▼).
Figure 6B:
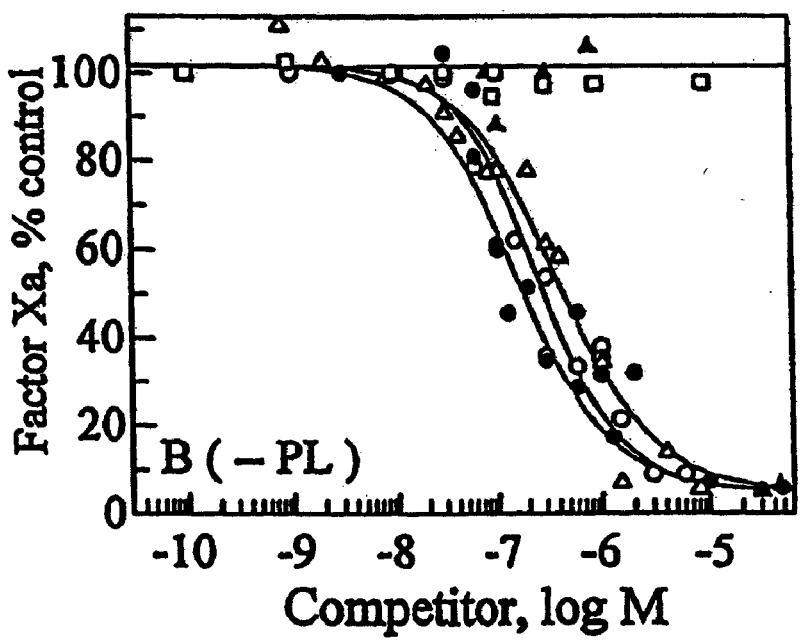
FIG. 6B depicts the inhibition of factor Xa generation by the active-site blocked (DEGR) EGF1 domain IXa mutants in the absence of phospholipid, where the symbols for the IXa proteins are the same as in FIG. 6A.

In the $Ca^{2+}$/phospholipid system (same conditions as in FIG. 2A, i.e., 20 nM IXa and 100 nM X), $IXa_{Q50P}$ activated factor X at 0.07 nM/min and $IXa_{PCEGF1}$ at 0.06 nM/min. These rates are slightly slower than the rate (0.1 nM/min) obtained with $IXa_{WT}$. These results could be attributed to a slight shift in the active site of the variant proteins relative to the EGF1 domain (Krishnaswamy, supra). When limiting concentrations of factor VIIIa in the complete Tenase system (VIIIa 70 pM, IXa 0.5 nM, and X 15 nM) were employed, both the EGF1 domain mutants failed to activate factor X at measurable rates (FIG. 5A and Table 1). As expected, both EGF1 domain mutants activated factor X in the presence of only $Ca^{2+}$ at rates similar to that of $IXa_{WT}$. Thus at 1 µM X and 400 nM IXa, the rates of activation by $IXa_{WT}$, $IXa_{Q50P}$ and $IXa_{PCEGF1}$ were ~0.46 nM/min, ~0.39 nM/min, and ~0.48 nM/min, respectively. Surprisingly, however, both mutants also activated factor X in the $Ca^{2+}$/VIIIa system at rates similar to that of $IXa_{WT}$ (FIG. 5B and Table 1). Consistent with these observations, Kd,app of IXa:VIIIa interaction was only impaired in the presence of phospholipid (FIG. 6A) and not in its absence (FIG. 6B). Kd,app values both in the presence and absence of phospholipid are provided in Table 1. In control experiments neither protein C nor DEGR-activated protein C competed with IXa in binding to VIIIa (FIGS. 6A and 6B). These data demonstrate that the EGF1 domain of factor IXa in the absence of phospholipid does not play a significant role in its interaction with VIIa and that in the presence of phospholipid it may primarily function to correctly position the protease domain for optimal binding to VIIIa.

Initial evidence which led to the proposal that the protease domain of factor IXa is involved in binding to factor VIIIa came from the observations that a MAb to the protease domain inhibited factor IXa:factor VIIIa interaction (Bajaj, 1985, supra). Additional biochemical studies supported this concept (Astermark et al., supra; O'Brien et al., supra). Further studies mapped this antibody to residues 180–310 of protease domain (Frazier et al., 1989, *Blood* 74, 971–977.) and a part of the epitope was found to be located in the calcium binding loop (Bajaj et al., 1992, supra). Moreover, a hemophilia B patient in which Glu-245 in factor IX, a ligand for $Ca^{2+}$-binding in the protease domain, was replaced by valine has been identified (Ludwig et al., 1992, *Blood* 79, 1225–1232). Based upon these studies, it was thought that the protease domain $Ca^{2+}$-binding loop may constitute a part of the factor VIIIa binding site (Id.). However, site-specific mutations adjoining this loop did not lead to impairment in the clotting activity of factor IX indicating that the $Ca^{2+}$-binding loop does not directly contribute to factor VIIIa binding (Hamaguchi et al., supra). Currently, it is believed that the binding of $Ca^{2+}$ to the protease domain indirectly affects binding of factor VIIIa to this domain (Mathur et al., 1997, supra).

Figure 7A:
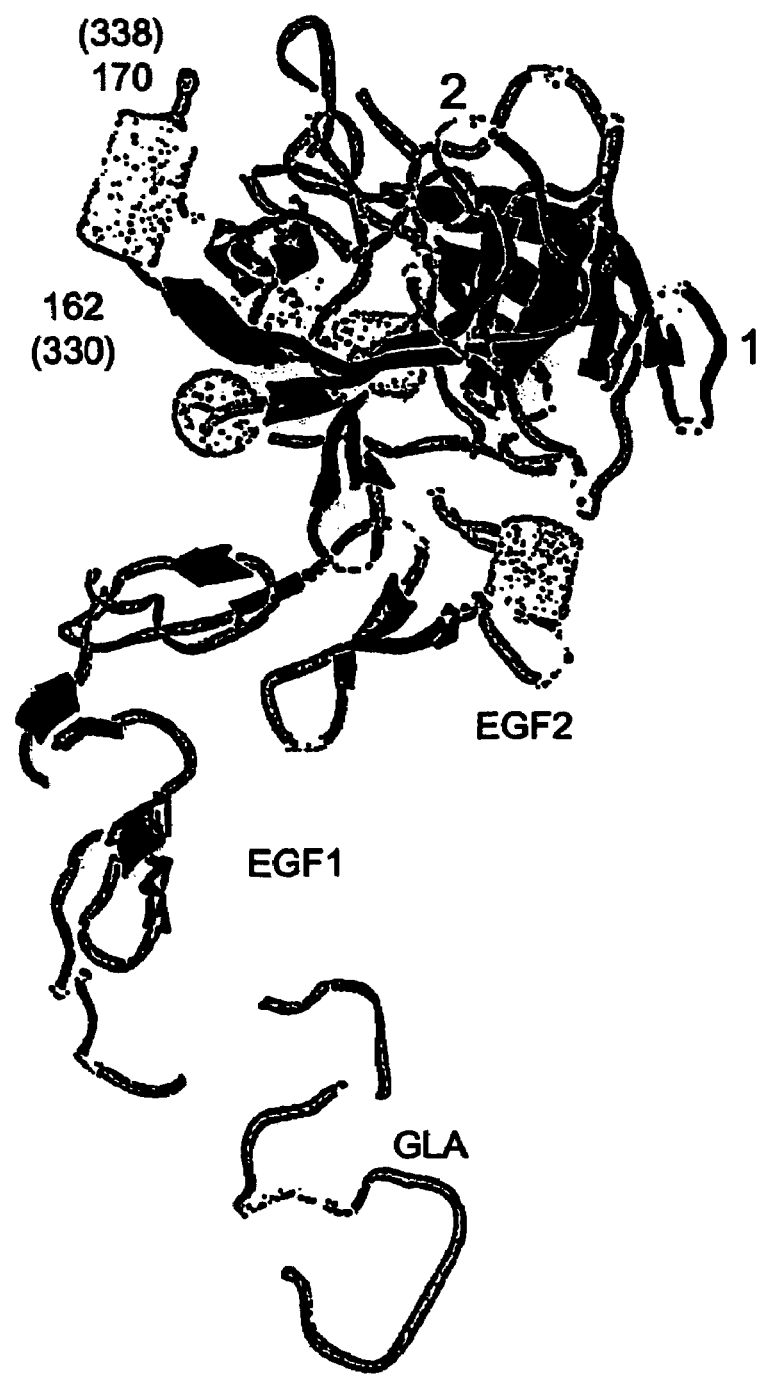
FIG. 7A depicts the position of various regions of factor IXa, including the helix-330 [162 chymotrypsin], where the protease domain Ca$^{2+}$-binding loop is marked number 1 and the autolysis loop is marked number 2.

In order to identify the region in the protease domain for IXa:VIIIa interaction, the role of surface-exposed helix-330 was studied, as reported above. The position of this helix is shown in FIG. 7A. The sequence in this helix is identical in factor IX from all species (Bajaj et al., 1993, supra) and is different from all other homologous blood coagulation serine proteases (Table 2). Further, helix-330 is located 12 residues away from the autolysis loop cleavage site to which it is connected via a single β-strand, marked 2 in FIG. 7A. Moreover, point mutations in eight of the nine residues in this helix are reported to cause hemophilia B (Giannelli et al., 1998, *Nucleic Acids Res.* 26, 265–268).

To further evaluate structural aspects of the regions investigated herein, a modeled structure of human factor IXa was obtained using a homology model building approach described earlier (Bajaj, 1993, supra). The starting template used was the structure of porcine factor IXa (Ref. 2, code 1 PFX). Since the model structure of human factor IXa for all purposes as it relates to this paper was the same as porcine factor IXa and the residues involved at the mutational sites are identical between the two proteins, the X-ray structure of porcine factor IXa was also utilized for analysis of the above data. The model of $IXa_{PCEGF1}$ protein was constructed by replacing the EGFI domain of factor IXa with that of activated protein C (Mather et al., 1996, *EMBO J*. 15, 6822–6831) and is more fully described in Bajaj, 1999, *Thrombos. Haemostas*.82:1663–1672, incorporated herein by reference.

Figure 7B:
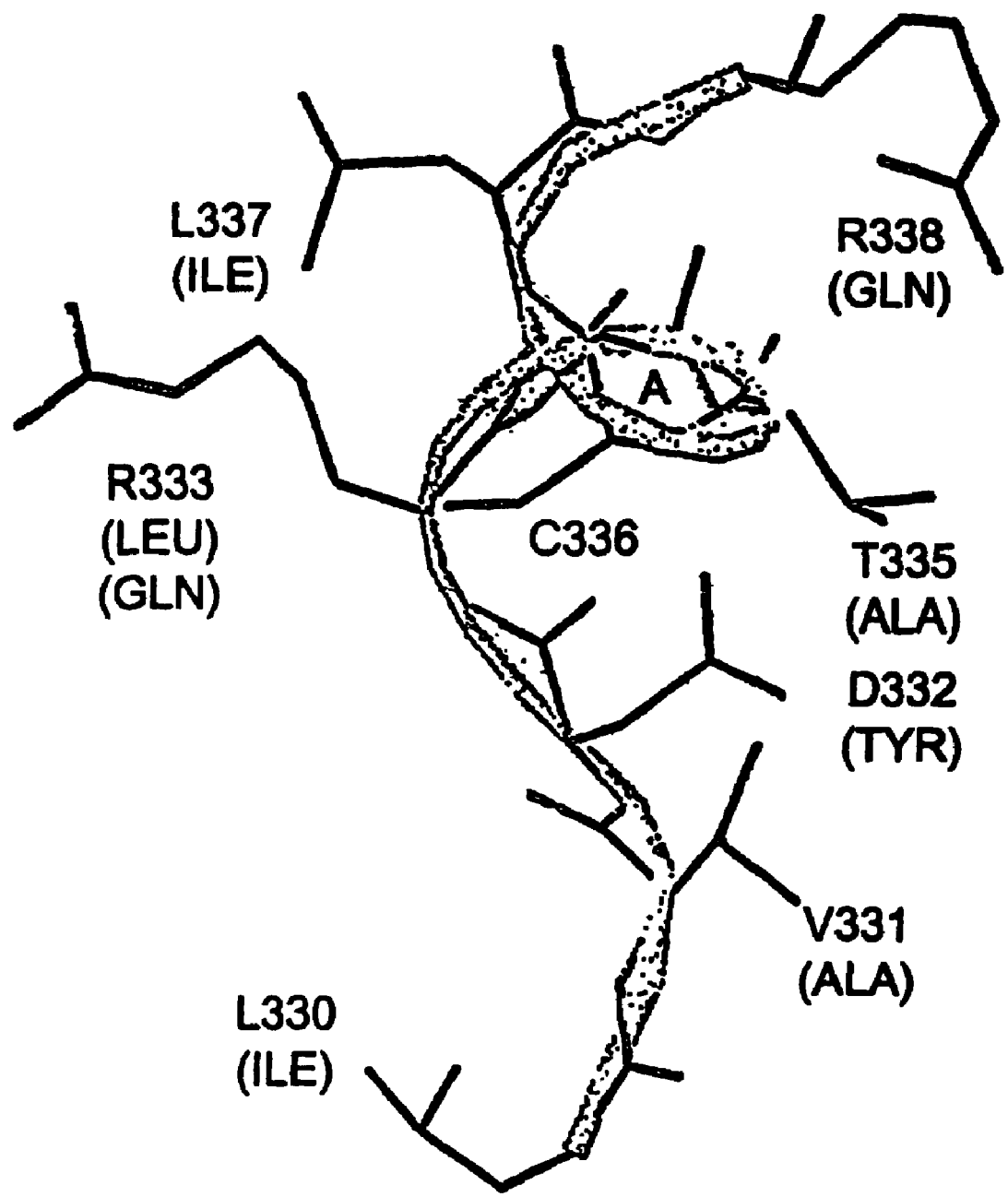
FIG. 7B depicts the orientation of the amino acid side chains of the helix-330 [162] of protease domain of factor IXa, where the point mutants investigated in the present study are given in parenthesis, and where the direction of the helix is from bottom to top.
Figure 8A:
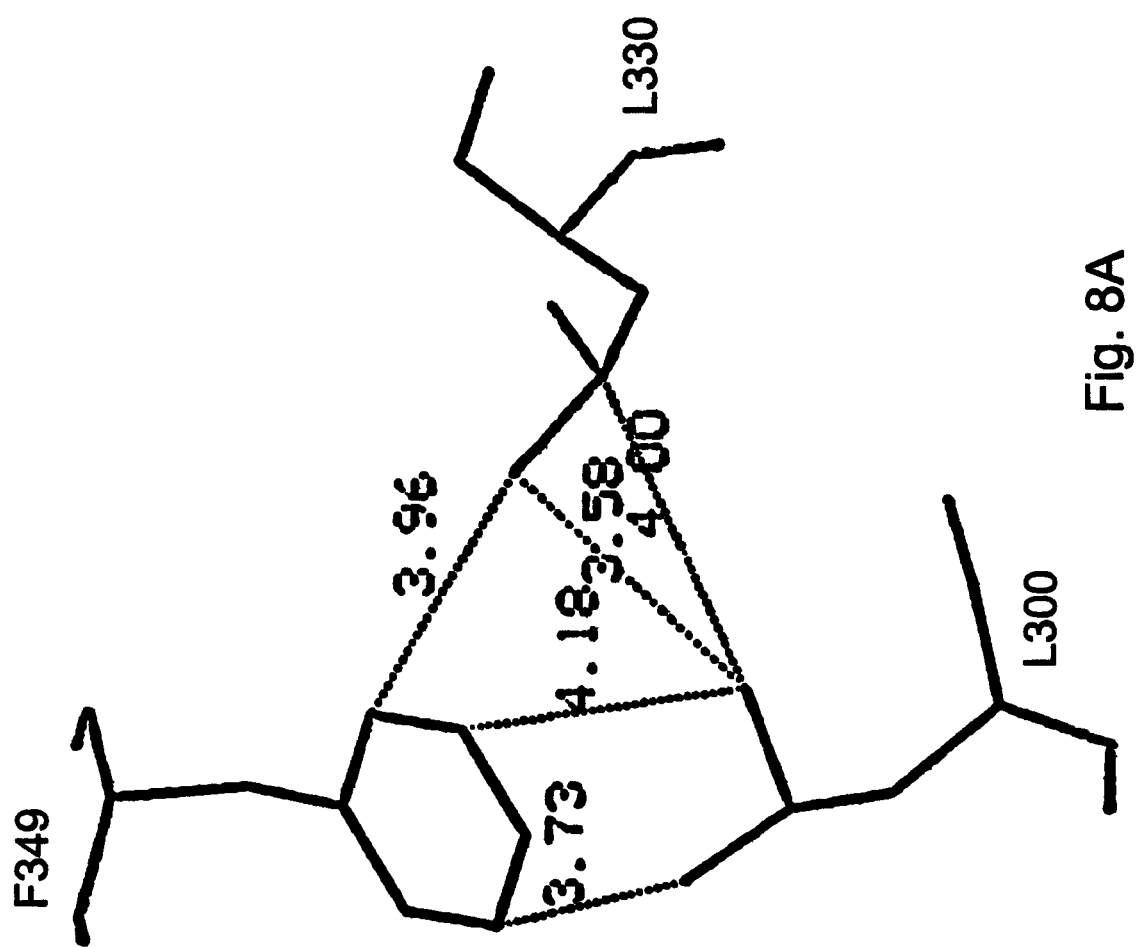
FIG. 8A depicts a schematic representation of the interactions and location of factor IXa residue L330[162] in a hydrophobic pocket surrounded by F349[181] and L300 [131], where the van der Waals contact distances (Å) are shown by dashed lines.
Figure 8B:
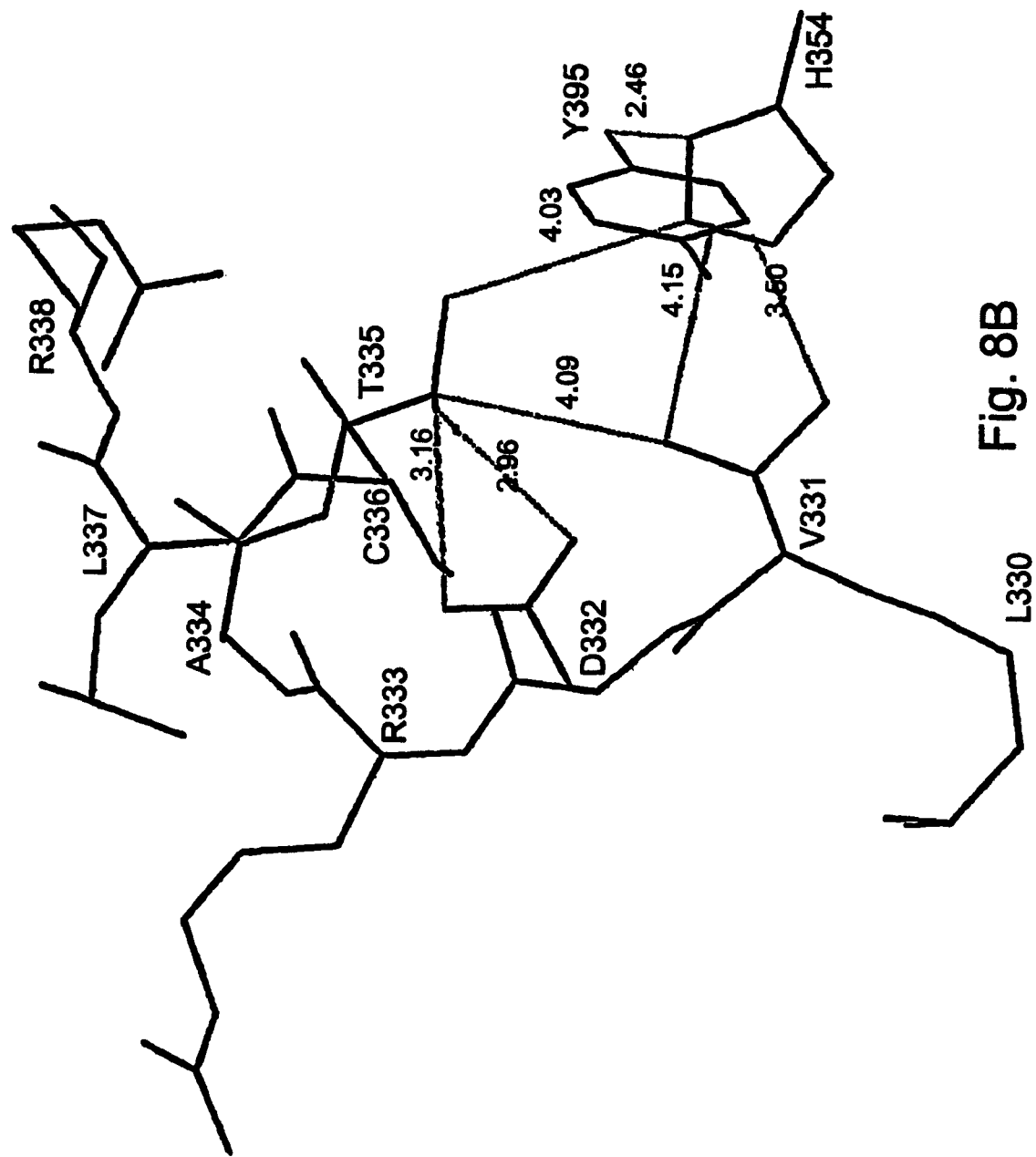
FIG. 8B depicts a schematic representation of the interactions of residues V331[163], D332[164], and T335[167] of factor IXa protease domain, where both the hydrogen bonds and the van der Waals contacts are shown by dashed lines.
Figure 8C:
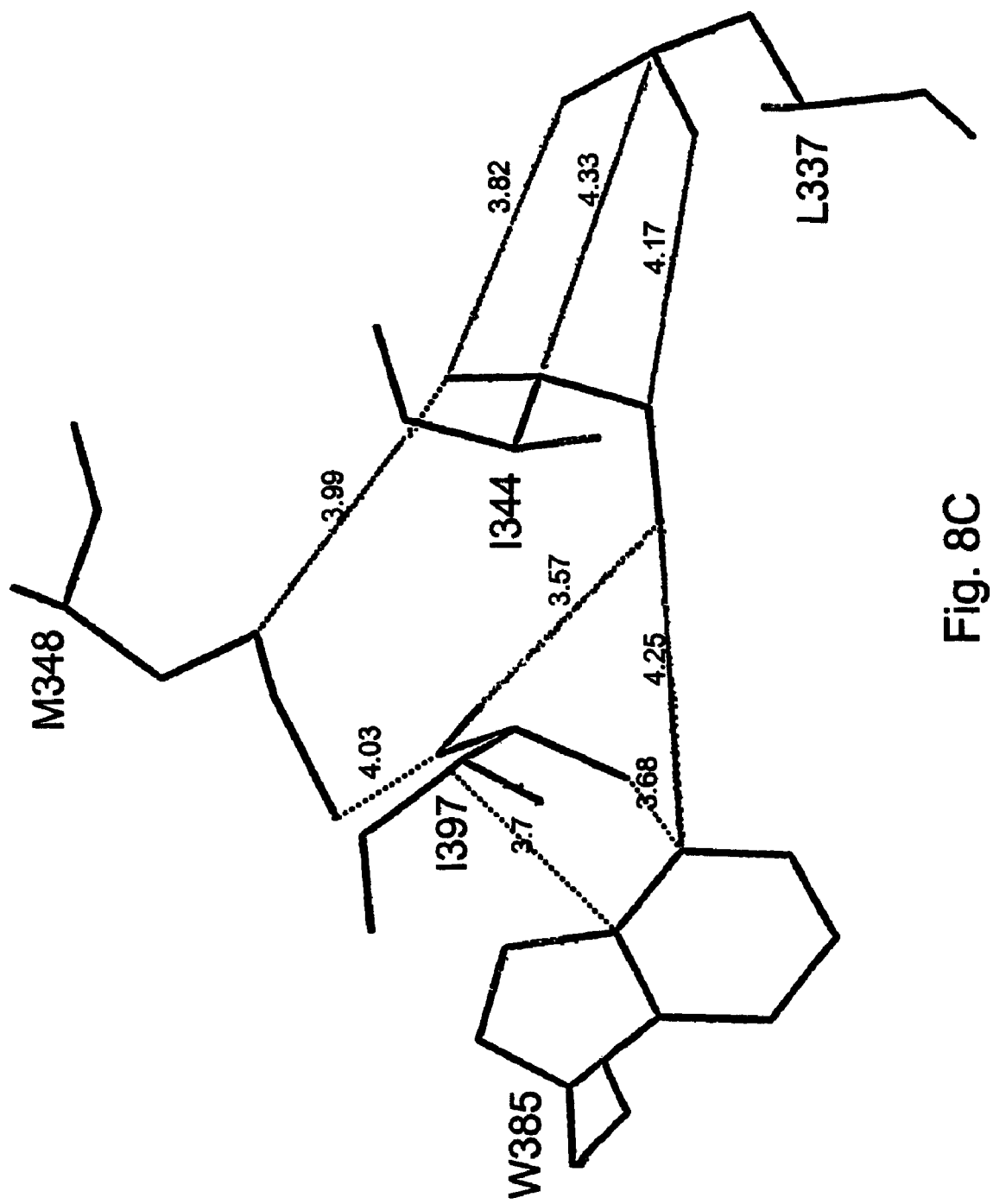
FIG. 8C depicts a schematic representation of the location and interactions of factor IXa residue L337[169] in a hydrophobic pocket, where the van der Waals distances of residues located in this hydrophobic pocket are shown by dashed lines.
Figure 8D:
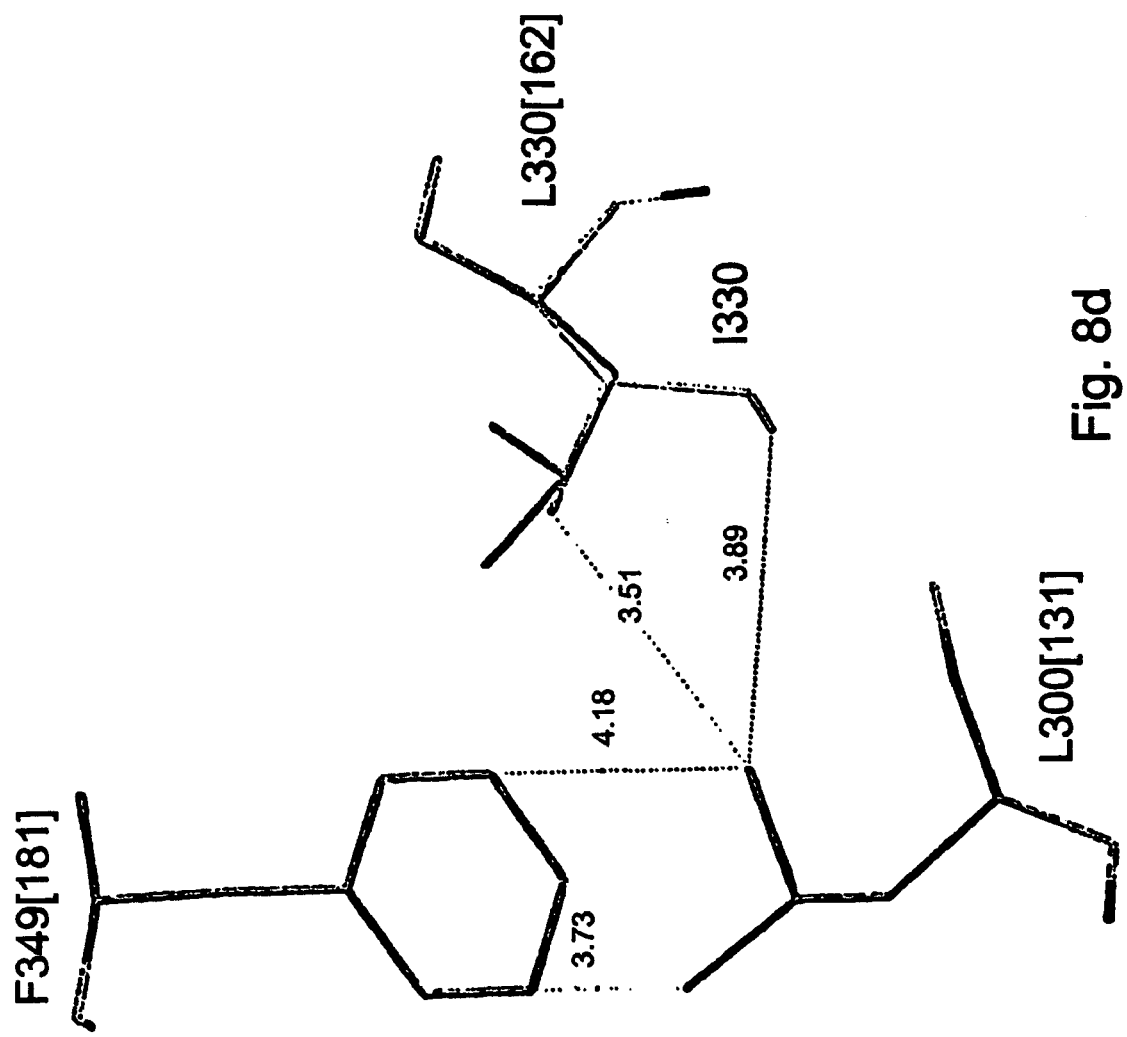
FIG. 8D depicts a schematic representation of the effect of the factor IXa mutation of L330 to I330 in a patient with hemophilia B, where the hydrophobic interaction between I330 with F349 which is present in wild-type factor IXa (FIG. 8A), is eliminated.
Figure 9:
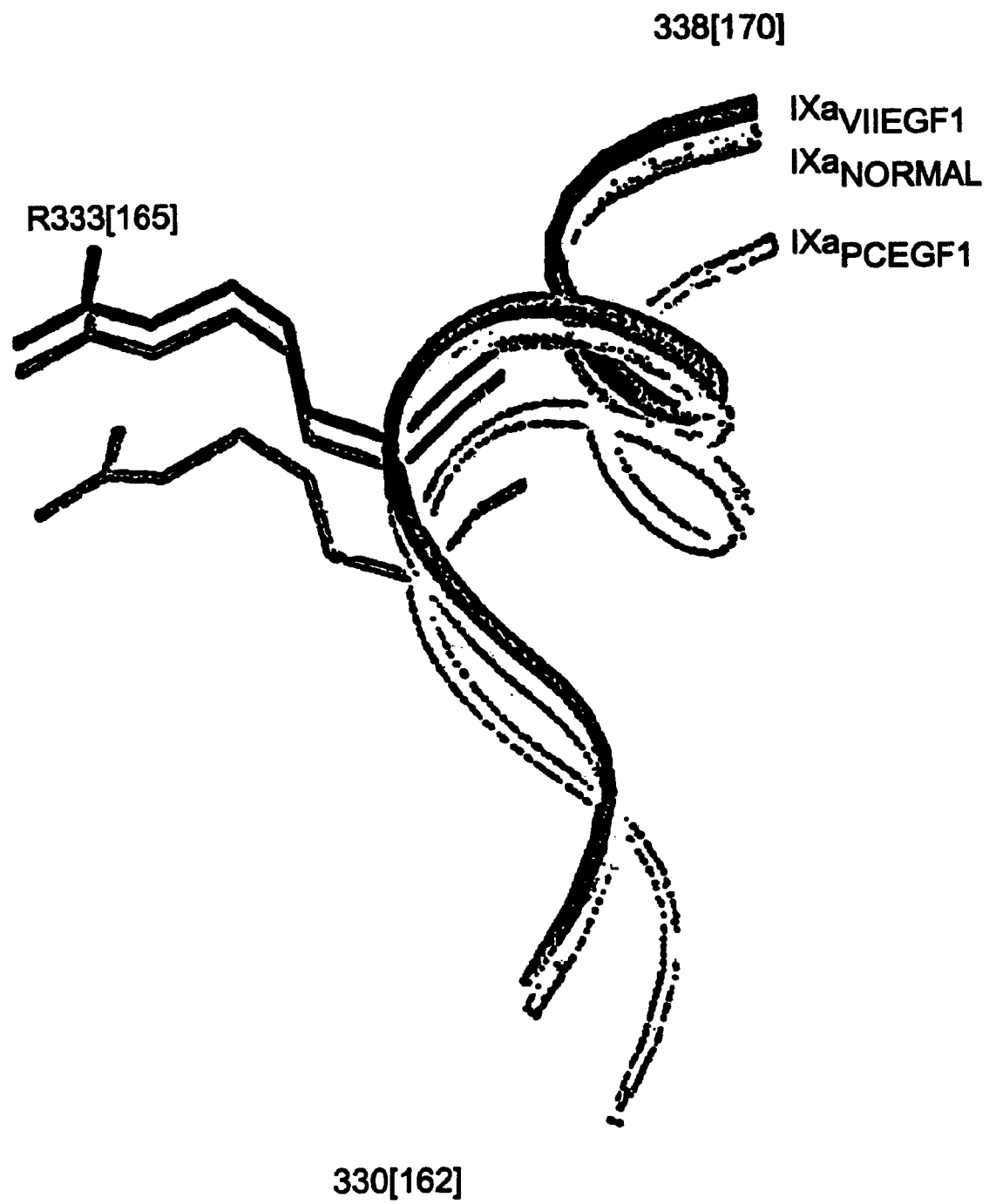
FIG. 9 depicts a schematic representation of the relative positions of the helix-330 in IXa$_{PCEGF}$ and IXa$_{VIIEGF1}$ with respect to its position in normal IXa.
Figure 10:
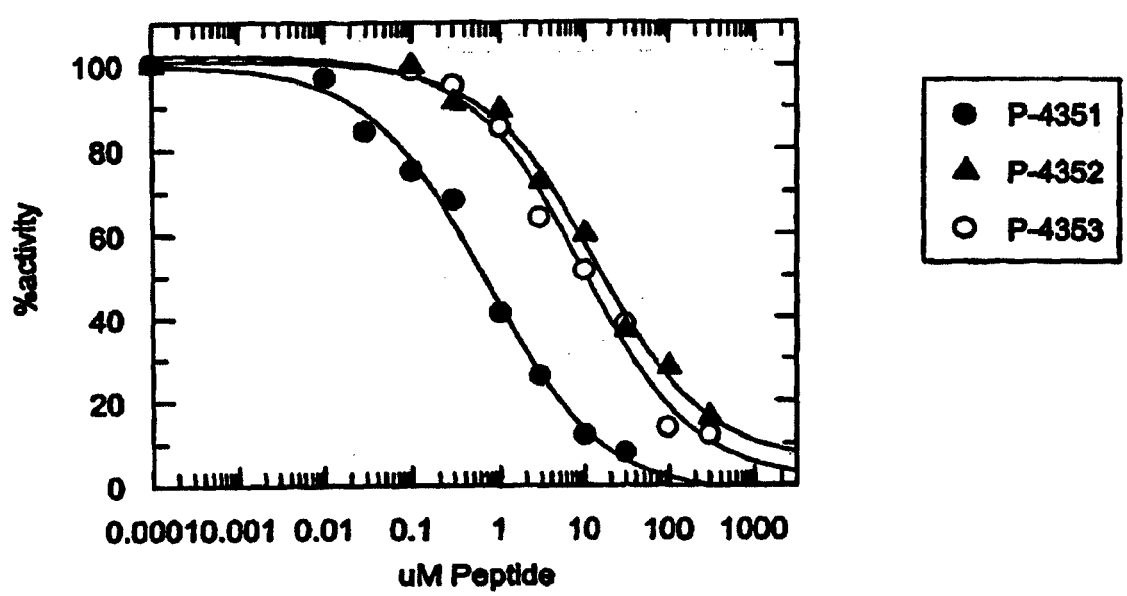
FIG. 10 depicts the inhibition of factor X activation by SEQ ID NO: 6 (LVDRAT), SEQ ID NO:7 (LVYRAT), and SEQ ID NO:8 (LVDQAT).
Figure 11:
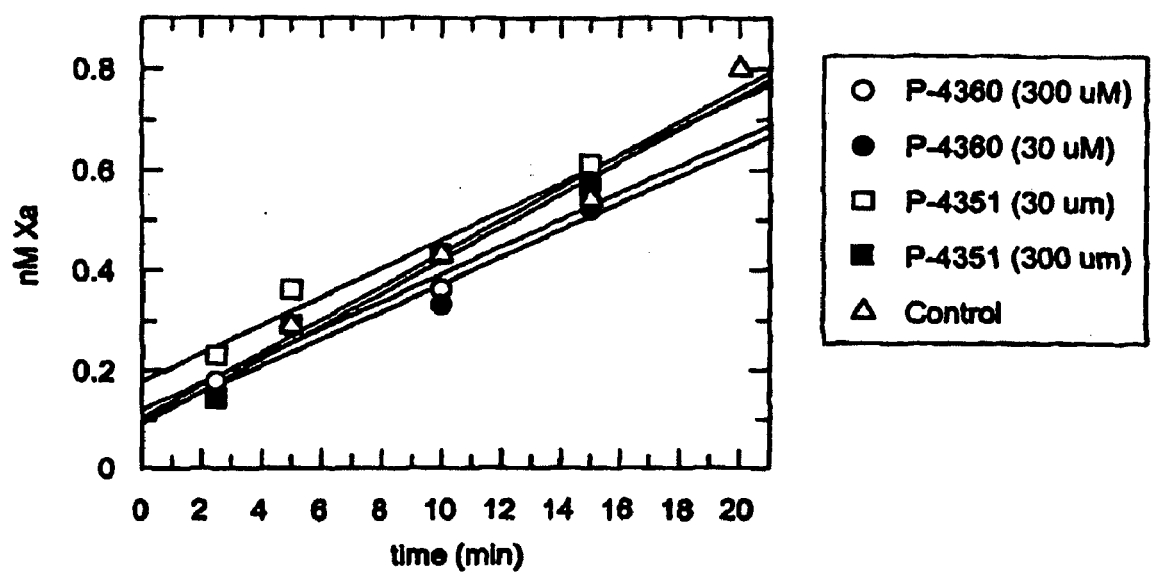
FIG. 11 demonstrates that the peptide of SEQ ID NO:6 has no inhibitory effect on factor IXa's ability to activate factor X in the absence of factor VIIIa.

The nature and orientation of the side chains along with the point mutants constructed in the present study are shown in FIG. 7B. All point mutants (except for R338Q) constructed in the helix-330 residues primarily based upon hemophilia B patients had reduced affinity for factor VIIIa both in the presence and absence of phospholipid (Table 1). Residue L330 [chymotrypsin 162] is located in a hydrophobic pocket (FIG. 8A) and makes van der Waals contacts with residues L300[131] and F349[181]. In the mutant L330I, the hydrophobic contacts with F349[181] may be weakened, since the hydrophobic interactions of I330 with F349 is eliminated by that mutation (FIG. 8D), which could destabilize the helix resulting in a reduced affinity for factor VIIIa. Residues V331[163], D332[164], and T335[167] are on the same side of the helix. The van der Waals and hydrogen bond interactions involving these residues are shown in FIG. 8B. When V331 [163] is changed to A331 [163], the hydrophobic contacts involving this residue with T335[167], H354[185] and Y395[225] will be weakened. This again will destabilize the helix resulting in an impaired interaction with factor VIIIa (Table 1). A change in D332 [164] to Y332[164] will disrupt essentially all contacts in this pocket since tyrosine is a much bulkier residue than aspartic acid which is expected to shift the helix away from the this pocket. Finally, a change of T335[167] to A335 will result in disruption of its contacts with D332, V331, and H354. Residue R333[165] is solvent exposed and abolishing the positive charge by mutational change may abolish the direct interaction of this amino acid with factor VIIIa. As depicted in FIG. 8D, change of L337[169] to I337 may result in the disruption of another hydrophobic pocket and a slight shift of the helix. Notably, change of R338[170] to Q338 [170] resulted in a minimal loss of biologic activity and affinity for factor VIIIa (Table 1). This is consistent with a slightly increased activity of R338A mutant without an impairment in factor VIIIa binding described by Chang and coworkers (Chang et al., 1998, *J. Biol. Chem.* 273, 12089–12094). Note that all of the helix-330 point mutants have impaired interaction with factor VIIIa both in the presence and absence of phospholipid. Furthermore, $IXa_{helixVII}$ mutant failed to interact with factor VIIIa even at very high concentrations both in the presence or absence of phospholipid. These data strongly support the conclusion that helix-330 in IXa represents a critical binding site for VIIIa.

Hemophilia B mutants not expressed in the present study in the helix-330 may have impaired interactions with factor VIIIa due to the following reasons. A change of L330[162] to proline may result in a turn accompanying a subtle directional change in the propagation of the helix, and a change of V331 [163] to aspartic acid is expected to disrupt the hydrophobic interactions depicted in FIG. 8B. Replacement of R333[165] by glycine, and of A334[166] by aspartic acid or threonine could disrupt the direct binding of factor IXa to factor VIIIa. A change of C336 to any other residue will disrupt the disulfide bond and a possible change in the local tertiary structure. Replacement of L337[168] to phenylalanine or proline is expected to disrupt the putative hydrophobic pocket (FIG. 8C) and in the case of the proline mutant, it may also change the direction of the polypeptide. Similarly, a change of R338 to proline could result in the change of the direction of the polypeptide and disruption of the local tertiary structure.

The first EGF-like domain of factor IXa has also been implicated in binding to factor VIIIa (Lenting et al., supra; Rees et al., supra; Hughes et al., supra). In the present study two EGF1 mutants were examined for their abilities to bind to factor VIIIa both in the presence and absence of phospholipid. In a system containing phospholipid, $IXa_{Q50P}$ and $IXa_{PCEGF1}$ interacted with factor VIIIa with ~20 and ~100 fold reduced affinity, respectively. However, in the absence of phospholipid, both activated mutants interacted with factor VIIIa with Kd,app indistinguishable from that of normal IXa (Table 1). Since alterations of the EGF1 domain affect VIIIa binding only in the presence of phospholipid but not in its absence whereas mutations in the helix-330 affect VIIIa binding in both the presence and absence of phospholipid, it can be concluded that helix-330 in IXa provides a crucial binding site for VIIIa and that the EGF1 domain in this context primarily serves to correctly position the protease domain above the phospholipid surface for optimal interaction with VIIIa.

Modeling studies support the concept that helix residues 330–338 may be shifted in the $IXa_{PCEGF1}$ mutant (FIG. 9). In this model, in which the membrane binding Gla domain coordinates are unchanged from normal IXa, the EGF2/protease domain coordinates including the helix-330 are shifted ~1.5 Å. Further, the eight-residue insertion in the EGF1 domain lies on the same side as the helix-330. As a consequence of these two deviations from normal IXa, it is possible that the interactions of the helix-330 residues with factor VIIIa are weakened. In other studies in which EGF1 domain of factor IX was replaced by that of factor X (Lin et al., 1990, *J. Biol. Chem.* 265, 144–150) or Factor VII (Chang et al., 997, *J. Clin. Invest.* 100, 886–892), the resulting molecule either had normal activity ($IXa_{XEGF1}$) or four-fold increased activity ($IXa_{VIIEGF1}$). The increased activity in the $IXa_{VIIEGF1}$ was attributed to the increased affinity of this mutant for factor VIIIa. When EGF1 domain of factor VII was modeled into the factor IX molecule, the EGF2/protease domain coordinates including those of the helix-330 were only shifted ~0.5 Å (FIG. 9). Further, this shift in $IXa_{VIIEGF1}$ was in the opposite direction to that observed in the $IXa_{PCEGF1}$ molecule. Since subtle changes can lead to increase in the bond strengths, it is possible that helix-330 residues in $IXa_{VIIEGF1}$ molecule are positioned more favorably to interact with factor VIIIa binding site. Furthermore, it is quite feasible that in other EGF1 mutants (Lenting et al., supra; Spitzer et al., 1990, *Blood* 151, 1530–1537; Rees et al., supra; Hughes et al., supra; McCord et al., 1990, *J. Biol. Chem.* 265, 10250–10254; Christophe et al., 1998, J. Biol. Chem. 237, 222–227.) and in a Gla domain mutant (Larson et al., 1996, *J. Biol. Chem.* 271, 3869–3876), the alignment of the helix-330 above the phospholipid surface is altered, which results in its impaired interactions with factor VIIIa. These conclusions are consistent with the observation of Lenting et al (supra) and of Christophe et al (supra) in which the light chain mutants of IXa, in the absence of phospholipid, have minimal alterations (2- to 4-fold) in direct binding to factor VIIIa, whereas in the presence of phospholipid interactions of these IXa variants with VIIIa were impaired 50- to 200-fold. As is the case with IXa$_{Q50P}$ and IXa$_{PCEGF1}$ (Table 1), it would be anticipated that interactions of the above mutants with factor VIIIa in the absence of phospholipid may be minimally impaired.

TABLE 1

Effect of factor VIIIa on the rates of factor X activation and Kd, app values for the interaction of various factor IXa proteins with factor VIIIa. The data of FIGS. 2, 3 and 5 were used for factor X activation rates. The conditions in the presence of phospholipid (PL-plus system) were 70 pM VIIIa, 0.5 nM IXa, and 15 nM X and the conditions in the absence of phospholipid (PL-minus system) were 14 nM VIIIa, 2 nM IXa, and 400 nM factor X. Kd, app values were calculated from FIGS. 4 and 6. NM, not measurable.

| | PL-plus system | | PL-minus system | |
|---|---|---|---|---|
| Protein | X-activation rate (nM/min) | Kd, app (nM) | X-activation rate (nM/min) | Kd, app (µM) |
| IXa$_{WT}$ or IXa$_{NP}$ | 2.6 ± 0.19 | 0.055 ± 0.01 | 2.75 ± 0.21 | 0.19 ± 0.02 |
| Protease domain mutants | | | | |
| IXa$_{L330I}$ | 0.95 ± 0.07 | 0.23 ± 0.05 | 0.94 ± 0.03 | 0.72 ± 0.07 |
| IXa$_{V331A}$ | 0.55 ± 0.04 | 0.61 ± 0.08 | 0.54 ± 0.02 | 1.35 ± 0.31 |
| IXa$_{D332Y}$ | NM | 2.86 ± 0.65 | NM | 5.13 ± 0.08 |
| IXa$_{R333L}$ | NM | 8.21 ± 1.7 | NM | 12.73 ± 2.52 |
| IXa$_{R333Q}$ | NM | 7.15 ± 1.2 | NM | 7.79 ± 0.75 |
| IXa$_{T335A}$ | 1.92 ± 0.11 | 0.14 ± 0.01 | 1.83 ± 0.18 | 0.46 ± 0.13 |
| IXa$_{L337I}$ | NM | 5.05 ± 0.89 | NM | 6.18 ± 0.62 |
| IXa$_{R338Q}$ | 2.53 ± 0.21 | 0.077 ± 0.01 | 2.22 ± 0.15 | 0.21 ± 0.03 |
| IXa$_{helixVII}$ | NM | NM | NM | NM |
| EGF1 domain mutants | | | | |
| IXa$_{Q50P}$ | NM | 1.25 ± 0.28 | 2.81 ± 0.25 | 0.21 ± 0.02 |
| IXa$_{PCEGF1}$ | NM | 5.71 ± 0.82 | 2.71 ± 0.27 | 0.21 ± 0.01 |

TABLE 2

Sequence of helix-330 in vitamin K dependent four coagulant and one anticoagulant (Protein C) serine proteases. The sequence of helix-330 is identical in factor IX from human, bovine, porcine, canine, rabbit, sheep, guinea pig, mouse and rat. For comparison, the residue number for each protein corresponding to residue 162 in chymotrypsin is given in parenthesis. A hyphen indicates the same residue as in factor IX. All sequences are taken from Bajaj and Birktoft, 1993, Methods Enzymol. 222, 96–128.

| Protein | Sequence | |
|---|---|---|
| | [162]          [170] | |
| Factor IX (330) | L V D R A T C L R | (SEQ ID NO: 1) |
| Factor VII (304) | R L M T Q D - - Q | (SEQ ID NO: 12) |
| Factor X (344) | Y - - - N S - K L | (SEQ ID NO: 13) |
| Prothrombin (487) | I - E - P V - K D | (SEQ ID NO: 14) |
| Protein C (325) | V - P H N E - S E | (SEQ ID NO: 15) |

EXAMPLE 2

Activation of Factor VIII:

Factor VIII was activated at a concentration of 40 units/mL with 0.2 nM thrombin in TBS (Tris-HCl pH 7.4) containing 1 mg/mL BSA and 5 mM CaCl$_2$. The reaction was incubated at 37° C. for 2 minutes at which time hirudin was added.

Factor IX Peptide Competition Assay in the Presence of Factor VIIIa:

Each reaction contained 0.2 nM factor IXa, 480 nM factor X, 0.07 nM factor VIIIa, various concentrations of peptide, 10 µM phospholipid, and 5 mM CaCl$_2$ in TBS (Tris-HCl, pH 7.4) containing 1 mg/mL BSA. Each reaction was incubated for either 30, 60, 90, or 120 seconds and the reaction was stopped by adding 1.5 µL of 0.5 M EDTA and placed on ice. Forty µL of each reaction was added to 100 µL of TBS/BSA in a 96 well microtiter plate and S-2222 (Bz-Ile-Glu(γ-OR)-Gly-Arg-p-nitroanilide) (SEQ ID NO: 18) was added to a final concentration of 100 µM. The change in absorbance at 405 nM was then observed using a Bio Rad microplate reader.

Factor IX Peptide Competition Assay in the Absence of Factor VIIIa:

Each reaction mixture contained 20 nM of factor IXa, 100 nM of factor X, various concentrations of peptide, 25 µM of phospholipid, and 5 mM CaCl$_2$ in TBS/BSA. The reaction mixtures were incubated for 2.5, 5, 10, 15, and 20 minutes at 37° C. and were stopped with the addition of 1.5 µL of 0.5 M EDTA and placed on ice. Forty µL of each reaction was 5 added to 100 µL of TBS/BSA in a 96 well microtiter plate and S-2222 was added to a final concentration of 100 µM. The change in absorbance at 405 nM was then observed using a Bio Rad microplate reader.

TABLE 3

| Peptide | IC$_{50}$ (µM) |
|---|---|
| P-4488 SEQ ID NO: 2 (DRAT) | 89.8 ± 27 |
| P-4351 SEQ ID NO: 6 (LVDRAT) | 0.7 ± 0.2 |
| P-4352 SEQ ID NO: 7 (LVYRAT) | 13.2 ± 2.4 |
| P-4353 SEQ ID NO: 8 (LVDQAT) | 9.3 ± 3.4 |
| EGF1 Domain | 12 ± 3 |

TABLE 4

| Peptide | Kd (µM) |
|---|---|
| P-4488 SEQ ID NO: 2 (DRAT) | 44.9 ± 14 |
| P-4351 SEQ ID NO: 6 (LVDRAT) | 0.35 ± 0.1 |
| P-4352 SEQ ID NO: 7 (LVYRAT) | 6.6 ± 1.2 |
| P-4353 SEQ ID NO: 8 (LVDQAT) | 4.7 ± 1.7 |
| P-4354 SEQ ID NO: 16 (TKVSRYVN) | 1.0 ± 0.3 |
| EGF1 Domain | 6.0 ± 1.5 |

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

What is claimed is:

1. A polypeptide of from 6 to 20 amino acids capable of inhibiting the activation of factor X in the presence of coagulation factor VIIIa, said polypeptide comprising SEQ ID NO:5 (LVX$_1$X$_2$AT), wherein X$_1$ is tyrosine and X$_2$ is either arginine or glutamine or wherein X$_1$ is either aspartic acid or tyrosine and X$_2$ is glutamine.

2. The polypeptide of claim 1 wherein the polypeptide comprises, SEQ ID NO:7 or SEQ ID NO:8.

3. A polypeptide of from 9 to 20 amino acids capable of inhibiting the activation of factor X in the presence of coagulation factor VIIIa, said polypeptide comprising SEQ ID NO:9, provided that Xaa of SEQ ID NO:9 is not cysteine.

4. The polypeptide of claim 3 wherein the polypeptide comprises SEQ ID NO:10.

5. A composition having anticoagulation activity wherein the composition comprises a polypeptide of from 6 to 20 amino acids capable of inhibiting the activation of factor X in the presence of coagulation factor VIIIa, said polypeptide comprising SEQ ID NO:5 (LVX$_1$X$_2$AT), wherein X$_1$ is tyrosine and X$_2$ is either arginine or glutamine or wherein X$_1$ is either aspartic acid or tyrosine and X$_2$ is glutamine.

6. The composition of claim 5 wherein the polypeptide comprises SEQ ID NO:7.

7. The composition of claim 5 wherein the polypeptide comprises SEQ ID NO:8.

8. A composition having anticoagulation activity wherein the composition comprises a polypeptide of from 9 to 20 amino acids capable of inhibiting the activation of factor X in the presence of coagulation factor VIIIa, said polypeptide comprising SEQ ID NO:9, provided that Xaa of SEQ ID NO:9 is not cysteine.

9. The composition of claim 8 wherein the polypeptide is SEQ ID NO:10.

10. The polypeptide of claim 1, wherein said polypeptide further comprises a covalently attached detectable moiety.

11. The polypeptide of claim 10, wherein said detectable moiety is radioactive or fluorescent.

12. The polypeptide of claim 2, wherein said polypeptide further comprises a covalently attached detectable moiety.

13. The polypeptide of claim 12, wherein said detectable moiety is radioactive or fluorescent.

14. The polypeptide of claim 3, wherein said polypeptide further comprises a covalently attached detectable moiety.

15. The polypeptide of claim 14, wherein said detectable moiety is radioactive or fluorescent.

16. The polypeptide of claim 4, wherein said polypeptide further comprises a covalently attached detectable moiety.

17. The polypeptide of claim 16, wherein said detectable moiety is radioactive or fluorescent.

18. A six amino acid polypeptide capable of inhibiting the activation of factor X in the presence of coagulation factor VIII, said six amino acid polypeptide comprising SEQ ID NO:5 (LVX$_1$X$_2$AT), wherein X$_1$ is either aspartic acid or tyrosine and X$_2$ is either arginine or glutamine.

19. The polypeptide of claim 18, wherein said polypeptide further comprises a covalently attached detectable moiety.

20. The polypeptide of claim 19, wherein said detectable moiety is radioactive or fluorescent.

21. The six amino acid polypeptide of claim 18, wherein said six amino acid polypeptide comprises SEQ ID NO: 6 SEQ ID NO:7 or SEQ ID NO:8.

22. A six amino acid pojypeptide of capable of inhibiting the activation of factor X in the presence of coagulation factor VIII, said six amino acid polypeptide consisting of SEQ ID NO:6 (LVDRAT).

* * * * *